(12) United States Patent
Atwood et al.

(10) Patent No.: US 8,525,124 B2
(45) Date of Patent: Sep. 3, 2013

(54) DEVICE FOR PIPE INSPECTION AND METHOD OF USING SAME

(75) Inventors: Christopher C. Atwood, Pittsburgh, PA (US); Richard P. Juchniewicz, Pittsburgh, PA (US); Eric Kratzer, Pittsburgh, PA (US); Adam Slifko, Pittsburgh, PA (US); Philip Jake Johns, Pittsburgh, PA (US)

(73) Assignee: RedZone Robotics, Inc., Pittsburgh, PA (US)

( * ) Notice: Subject to any disclaimer, the term of this patent is extended or adjusted under 35 U.S.C. 154(b) by 646 days.

(21) Appl. No.: 12/611,641

(22) Filed: Nov. 3, 2009

(65) Prior Publication Data

US 2010/0218624 A1    Sep. 2, 2010

Related U.S. Application Data

(60) Provisional application No. 61/110,870, filed on Nov. 3, 2008.

(51) Int. Cl.
*F16L 101/30* (2006.01)
*F16L 55/32* (2006.01)
*B62D 55/06* (2006.01)
*G01N 21/88* (2006.01)
*G01N 21/954* (2006.01)

(52) U.S. Cl.
USPC .............. 250/394; 73/592; 73/601; 73/865.8; 73/866.5; 104/138.2; 356/72; 356/241.6

(58) Field of Classification Search
None
See application file for complete search history.

(56) References Cited

U.S. PATENT DOCUMENTS

| 3,562,642 A | 2/1971 | Hochschild |
| 3,672,785 A | 6/1972 | Byrne |
| 4,029,428 A | 6/1977 | Levens |
| 4,179,216 A | 12/1979 | Theurer et al. |
| 4,197,908 A | 4/1980 | Davis et al. |
| 4,431,017 A | 2/1984 | Willemsen |
| 4,437,526 A | 3/1984 | Gloor |
| 4,442,891 A | 4/1984 | Wood |
| 4,577,388 A | 3/1986 | Wood |
| 4,613,812 A | 9/1986 | Gelston, II |
| 4,630,676 A | 12/1986 | Long, Jr. |
| 4,648,454 A | 3/1987 | Yarnell |
| 4,675,604 A | 6/1987 | Moyer et al. |
| 4,701,988 A | 10/1987 | Wood |

(Continued)

FOREIGN PATENT DOCUMENTS

AT    397432           4/1994
DE    19627455 C1 *   1/1998

(Continued)

OTHER PUBLICATIONS

ISA Written Opinion.*

(Continued)

*Primary Examiner* — Thomas P Noland
(74) *Attorney, Agent, or Firm* — Ference & Associates LLC

(57) ABSTRACT

A device. The device includes a sensor portion and a chassis portion. The sensor portion includes a plurality of sensing devices. The chassis portion is connected to the sensor portion and includes a first track and a second track. The second track is positioned adjacent the first track. The first and second tracks cooperate to substantially cover an entire width of the chassis portion.

12 Claims, 21 Drawing Sheets

(56) References Cited

U.S. PATENT DOCUMENTS

| | | |
|---|---|---|
| 4,724,108 A | 2/1988 | Jurgenlohmann et al. |
| 4,725,883 A | 2/1988 | Clark et al. |
| 4,765,173 A | 8/1988 | Schellstede |
| 4,800,104 A | 1/1989 | Cruickshank |
| 4,819,721 A | 4/1989 | Long, Jr. |
| 4,822,211 A | 4/1989 | Shinoda et al. |
| 4,825,969 A * | 5/1989 | King et al. .................. 180/9.1 |
| 4,862,808 A | 9/1989 | Hedgcoxe et al. |
| 4,951,758 A | 8/1990 | Sonku et al. |
| 4,955,951 A | 9/1990 | Nemoto et al. |
| 5,018,545 A | 5/1991 | Wells |
| 5,044,824 A | 9/1991 | Long, Jr. et al. |
| 5,063,780 A | 11/1991 | Landry et al. |
| 5,088,553 A | 2/1992 | Ralston et al. |
| 5,105,882 A | 4/1992 | Ralston et al. |
| 5,150,989 A | 9/1992 | Long, Jr. et al. |
| 5,195,392 A | 3/1993 | Moore et al. |
| 5,197,540 A | 3/1993 | Yagi et al. |
| 5,272,986 A | 12/1993 | Smart |
| 5,315,770 A * | 5/1994 | Campbell ..................... 37/96 |
| 5,318,395 A | 6/1994 | Driver |
| 5,329,824 A | 7/1994 | Carapezza et al. |
| 5,387,092 A | 2/1995 | Pettitt et al. |
| 5,454,276 A | 10/1995 | Wernicke |
| 5,520,569 A | 5/1996 | Endoh |
| 5,565,633 A | 10/1996 | Wernicke |
| 5,571,977 A | 11/1996 | Kipp |
| 5,574,223 A | 11/1996 | Kiefer |
| 5,577,864 A | 11/1996 | Wood et al. |
| 5,608,847 A | 3/1997 | Pryor |
| 5,700,110 A | 12/1997 | Kamiyama et al. |
| 5,736,821 A | 4/1998 | Suyama |
| 5,742,517 A | 4/1998 | Van Den Bosch |
| 5,773,984 A | 6/1998 | Suyama et al. |
| 5,794,431 A | 8/1998 | Utamura et al. |
| 5,878,783 A | 3/1999 | Smart |
| 5,892,163 A | 4/1999 | Johnson |
| 5,947,051 A | 9/1999 | Geiger |
| 5,947,213 A | 9/1999 | Angle et al. |
| 5,960,882 A | 10/1999 | Polivka |
| 5,975,878 A | 11/1999 | Wood et al. |
| 5,992,247 A | 11/1999 | Manestar |
| 6,026,911 A | 2/2000 | Angle et al. |
| 6,031,371 A | 2/2000 | Smart |
| 6,039,079 A | 3/2000 | Kiest, Jr. |
| 6,056,017 A | 5/2000 | Kamiyama et al. |
| 6,068,725 A | 5/2000 | Tweedie et al. |
| 6,082,411 A | 7/2000 | Ward |
| 6,141,810 A | 11/2000 | Allen et al. |
| 6,155,363 A | 12/2000 | Matsumoto et al. |
| 6,162,171 A | 12/2000 | Ng et al. |
| 6,173,562 B1 | 1/2001 | Utamura et al. |
| 6,175,380 B1 | 1/2001 | Van Den Bosch |
| 6,202,400 B1 | 3/2001 | Utamura et al. |
| 6,243,483 B1 | 6/2001 | Petrou et al. |
| 6,243,657 B1 | 6/2001 | Tuck et al. |
| 6,377,734 B1 | 4/2002 | Mayr et al. |
| 6,378,627 B1 | 4/2002 | Tubel |
| 6,386,797 B1 | 5/2002 | Gearhart |
| 6,405,798 B1 | 6/2002 | Barrett et al. |
| 6,427,602 B1 | 8/2002 | Hovis et al. |
| 6,431,270 B1 | 8/2002 | Angle |
| 6,446,718 B1 | 9/2002 | Barrett et al. |
| 6,450,104 B1 | 9/2002 | Grant et al. |
| 6,571,492 B2 * | 6/2003 | Greenwood ................... 37/348 |
| 6,661,524 B2 * | 12/2003 | Smith et al. ................... 356/614 |
| 6,684,706 B2 | 2/2004 | Knight et al. |
| 6,695,013 B2 | 2/2004 | Warren |
| 6,697,710 B2 | 2/2004 | Wilcox |
| 6,745,955 B2 | 6/2004 | Kronz |
| 6,843,317 B2 | 1/2005 | Mackenzie |
| 6,845,819 B2 | 1/2005 | Barrett et al. |
| 6,887,014 B2 | 5/2005 | Holland |
| 6,898,936 B1 | 5/2005 | Ochs et al. |
| 6,964,309 B2 | 11/2005 | Quinn et al. |
| 7,009,698 B2 | 3/2006 | Drost et al. |
| 7,042,184 B2 | 5/2006 | Oleynikov et al. |
| 7,053,391 B2 * | 5/2006 | Blume ..................... 250/559.02 |
| 7,069,124 B1 | 6/2006 | Whittaker et al. |
| 7,073,979 B2 | 7/2006 | McGrew et al. |
| 7,126,303 B2 | 10/2006 | Farritor et al. |
| 7,131,791 B2 | 11/2006 | Whittaker et al. |
| 7,137,465 B1 | 11/2006 | Kerrebrock et al. |
| 7,148,962 B2 | 12/2006 | Fuhrland et al. |
| 7,191,191 B2 | 3/2007 | Peurach et al. |
| 7,210,364 B2 | 5/2007 | Ghorbel et |
| 7,434,757 B2 | 10/2008 | Beckham |
| 7,460,980 B2 | 12/2008 | Hinn |
| 7,594,448 B2 | 9/2009 | Jacobson et al. |
| 7,680,625 B2 | 3/2010 | Trowbridge et al. |
| 8,225,667 B2 * | 7/2012 | Hanan et al. .................... 73/619 |
| 2002/0062177 A1 | 5/2002 | Hannaford et al. |
| 2003/0089267 A1 | 5/2003 | Ghorbel et al. |
| 2003/0164952 A1 | 9/2003 | Deichmann et al. |
| 2003/0172871 A1 | 9/2003 | Scherer |
| 2003/0198374 A1 | 10/2003 | Hagene et al. |
| 2003/0216836 A1 | 11/2003 | Treat et al. |
| 2004/0021858 A1 | 2/2004 | Shima et al. |
| 2004/0055746 A1 | 3/2004 | Ross et al. |
| 2004/0088080 A1 | 5/2004 | Song et al. |
| 2004/0175235 A1 | 9/2004 | Whittaker et al. |
| 2004/0211894 A1 | 10/2004 | Hother et al. |
| 2005/0104600 A1 | 5/2005 | Cotton |
| 2005/0228573 A1 | 10/2005 | Gangopadhyay |
| 2005/0288819 A1 | 12/2005 | de Guzman |
| 2006/0066847 A1 | 3/2006 | Penza |
| 2006/0074525 A1 | 4/2006 | Close et al. |
| 2006/0290779 A1 | 12/2006 | Reverte et al. |
| 2007/0131438 A1 * | 6/2007 | Brandt et al. ................. 172/464 |
| 2007/0153918 A1 | 7/2007 | Rodriguez |
| 2007/0234702 A1 | 10/2007 | Hagen et al. |
| 2008/0179115 A1 * | 7/2008 | Ohm et al. .................... 901/1 X |
| 2009/0037146 A1 | 2/2009 | Trowbridge et al. |
| 2010/0218624 A1 | 9/2010 | Atwood et al. |
| 2011/0026770 A1 * | 2/2011 | Brookshire ................... 382/103 |
| 2011/0037311 A1 * | 2/2011 | Stolkin et al. ................. 305/116 |
| 2012/0097461 A1 * | 4/2012 | Rudakevych ................. 901/1 X |
| 2012/0199407 A1 * | 8/2012 | Morey et al. .................. 901/1 X |
| 2012/0211287 A1 * | 8/2012 | Andrus et al. ................ 180/9.1 |
| 2012/0292120 A1 * | 11/2012 | Ben-Tzvi ...................... 180/9.1 |

FOREIGN PATENT DOCUMENTS

| | | | |
|---|---|---|---|
| EP | 462527 | 12/1991 | |
| GB | 1469215 A * | 4/1977 | |
| GB | 2091611 | 8/1982 | |
| GB | 2408340 A * | 5/2005 | |
| JP | 05131381 A * | 5/1993 | ........................ 901/1 |
| JP | 10286878 | 10/1998 | |
| WO | PCT/US2009/063129 | * 2/2010 | |

OTHER PUBLICATIONS

Remote Orbital Installations LLC, website, roi360.com/equipment, downloaded Oct. 2007, 4 pages.

Remote Orbital Installations LLC, TRANSPOD Product Brochure; date unknown , but by Jun. 2011, 3 pages.

Cues Inc., CUES-IMX Product Brochure; date unknown , but by Jun. 2011, 2 pages.

Cues Inc., Quick ZoomCam Product Brochure; date unknown, but at least 1st 2 of 4 pages downloaded Oct. 2007 at http://www.cuesinc.com/Quick-Zoom.html.

"EPA Collection Systems O&M Fact Sheet Sewer Cleaning and Inspection", United States Environmental Protection Agency, Office of Water, EPA 832-F-99-031, Sep. 1999, 11 pages.

Hirose, et al., "Design of In-Pipe Inspection Vehicles phi50, phi150 pipes", IEEE, pp. 2309-2314, 1999, Proceedings of the 1999 IEEE International Conference on Robotics & Automation, May 1999.

Kawaguchi et al., "An Efficient Algorithm of Path Planning for an Internal Gas Pipe Inspection Robot", IEEE, pp. 1155-1160, 1992 Proceedings of the 1992 IEEE/RSJ International Conference on Intelligent Robots and Systems, Jul. 1992.

Bertetto, et al., "Robot Flessibile a BAsso Costo Per Ispezioni Tuni", Internet, 2006 p. 1477, an abstract only.

Torbin, "Advanced Inspection Robot for Unpiggable Pipelines", Internet, pp. 1-9, 2006.

Jin-Wu et al., A Pipeline Inspection Micro Robot Based on Screw Motion Wheels Intervent, 2000, p. 235-238, Journal of Shanghai University (English Edition) ISSN 1007-6417, vol. 4, No. 3 (Sep. 2000).

Kawaguchi et al., Internal Pipe Inspection Robot, 1995, IEEE, p. 857-862, IEEE International Conference on Robotics and Automation 0-7803-1965-6/95.

Ryew et al., Inpipe Inspection Robot System with Active Steering Mechanism, 2000, IEEE, p. 1652-1657.

Ono et al., Development of an In-pipe Inspection Robot Movable for a Long Distance, 2001, Internet, p. 1-4, Proceedings of the 2000 IEEE/RSJ International Conference on Intelligent Robots and Systems.

Choi et al., Development of Articulated Robot for Inspection of Underground Pipelines, 1999, Internet, p. 407-414, Transactions of the 15th International Conference on Structural Mechanics in Reactor Technology (SMiRT-15), in August.

Grobmann et al., A Robot Control System Integrating Reactive Control, Reasonong, and Execution Monitoring, 2002, Internet p. 1-16, Technical Report WV-03-02/CL-2003-01.

Musliner et al., Execution Monitoring and Recovery Planning with Time, 1991, p. 1-4.

Jeng et al., Reliable Automated Manufacturing System Design Based on SMT Framework, 1998, Internet, p. 121-147, Computers in Industry 35.

Schempf et al., Neptune: Above-Ground Storage Tank Inspection Robot System, 1995, IEEE, p. 1-7, IEEE Robotics & Automation, Society Magazine, Issue: Jun. 1995.

Choi et al., Feeder Pipe Inspection Robot With an Inch-Worm Mechanism Using Pneumatic Actuators, International Journal of Control, Automation, and Systems, vol. 4, No. 1, Feb. 2006, p. 87-95.

Silva, Intelligent Control of Robotic Systems with Application in Industrial Process, 1997, p. 221-237, Robotics and Autonomous Systems 21.

Nitzan, Three-Dimensional Vision Structure for Robot Applications, IEEE, 1988, p. 291-309, IEEE Transactions on Pattern Analysis and Machine Intelligence, vol. 10, No. 3 in May.

Yamada et al., A Method of 3D Object Reconstruction by Fusing Vision with Touch Sensing Using Internal Models with Global and Local Deformations, IEEE, 1993, p. 782-787.

Gu et al., Interpretation of Mechanical Impedance Profiles for Intelligent Control of Robotic Meat Processing, IEEE, 1996, p. 507-512.

Jung et al., Adaptive Force Tracking Impedance Control of Robot for Cutting Nonhomogeneous Workpiece, IEEE, 1999, p. 1800-1805, proceedings of the 1999 IEEE International Conference on Robotics & Automation, in May.

Wang et al., Application of Force Control on the Working Path Tracking, Journal of Marine Science and Technology, vol. 10, No. 2, 2002, p. 98-103.

Xiao et al., Sensor-Based Hybrid Position/Force Control of a Robot Manipulator in an Uncalibrated Environment, IEEE, No. 4, Jul. 2099.

Lawson S.W. & Pretlove, Augmented Reality for Underground Pipe Inspection and Maintenance, Mechatronic Systems and Robotics Research Group, 1998, p. 1-7.

Roth H & Schilling K., Inspection and Repair Robots for Waste Water Pipes—A Challenge to Sensorics and Locomotion, IEEE, 1998, p. 476-478.

Schenker, Paul S., Advanced Man-Machine Interfaces and Control Architecture for Dexterous Teleoperations, IEEE, 1991, p. 1506-1525.

International Search Report for corresponding International Application PCT/US09/63129, Feb. 3, 2010 was mail date, 3 pages, no written opinion included.

Rokke, Pette, and Johan E. Hustad, "Exhaust Gas Recirculation in Gas Turbines for Reduction of CO2 Emissions; Combustion Testing with Focus on Stability and Emissions", Int. Journal of Thermodynamics, vol. 8, No. 4, pp. 167-173, Sep. 2005.

* cited by examiner

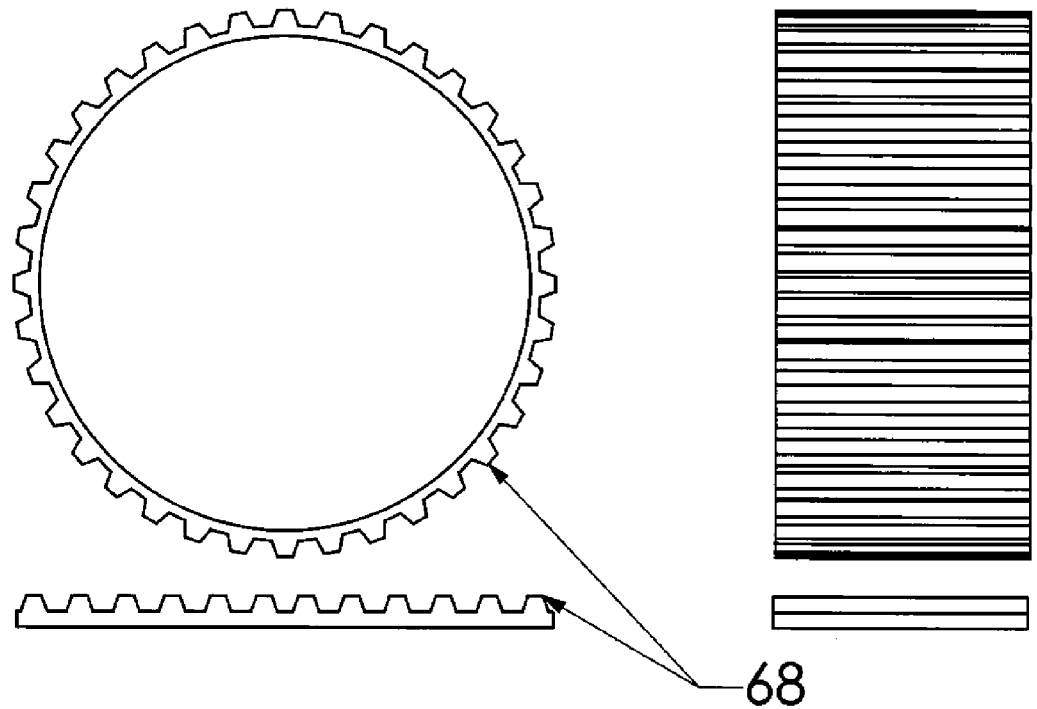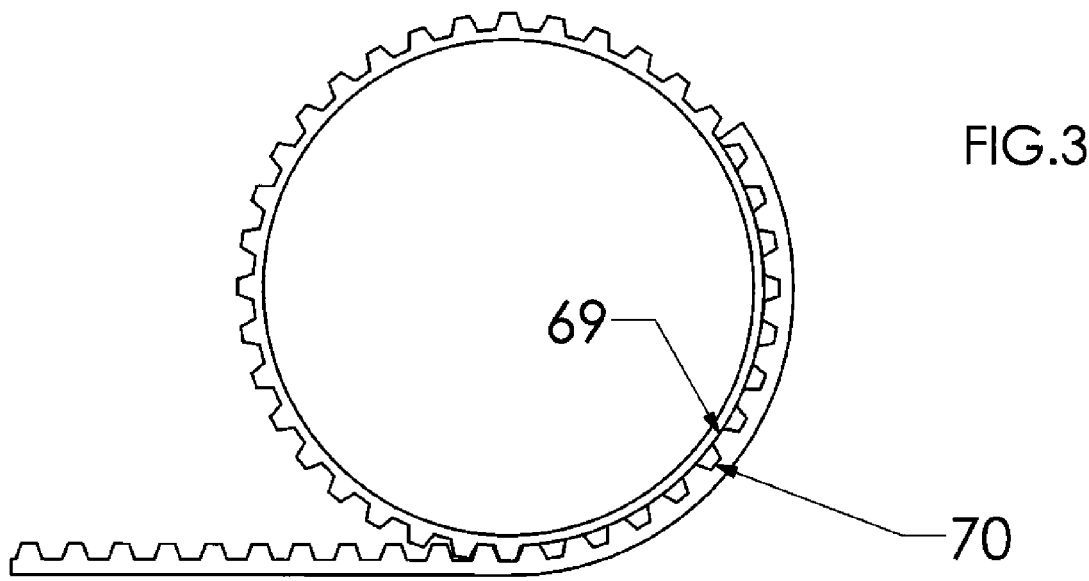
FIG.3

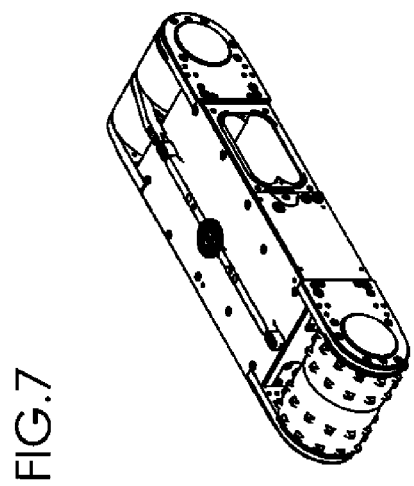
FIG.7
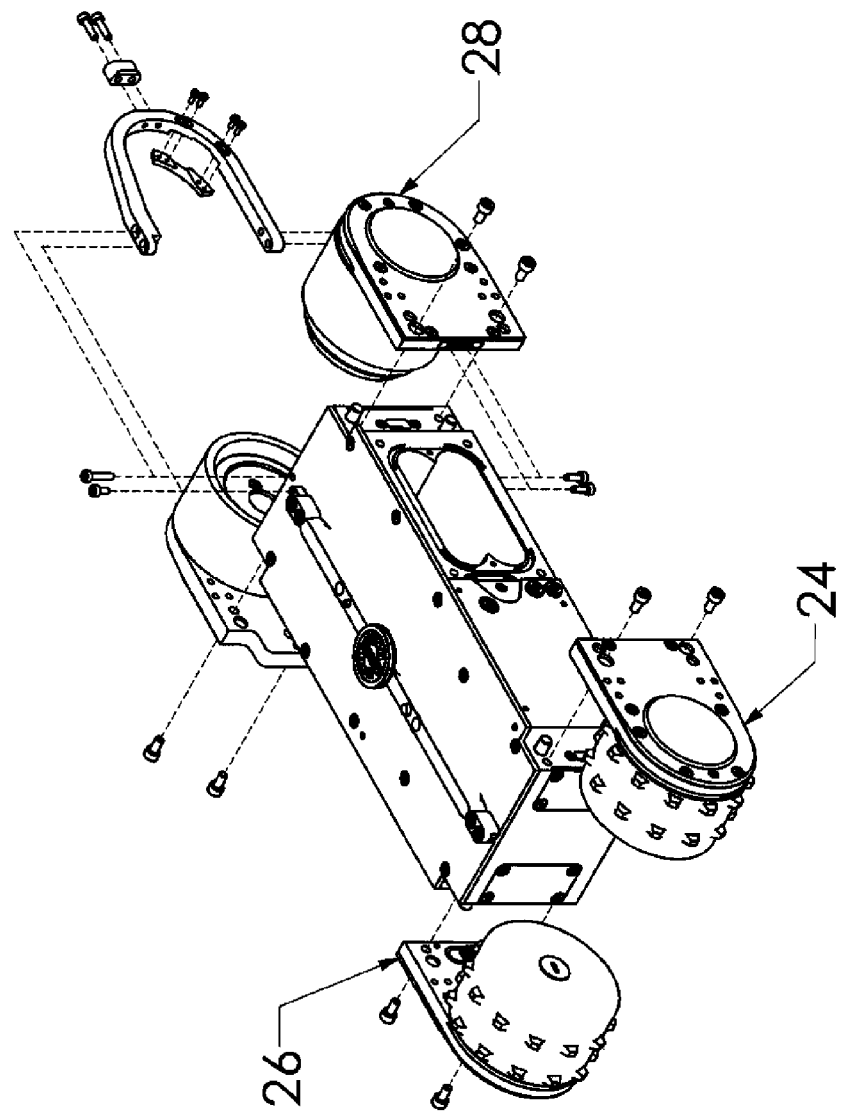

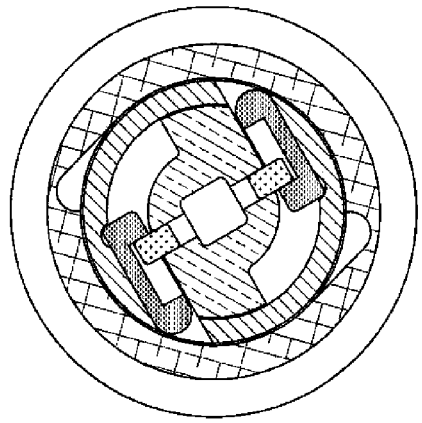
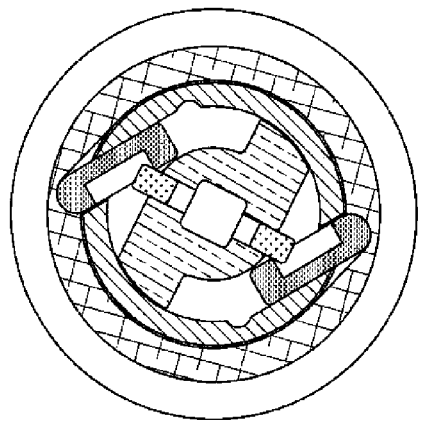
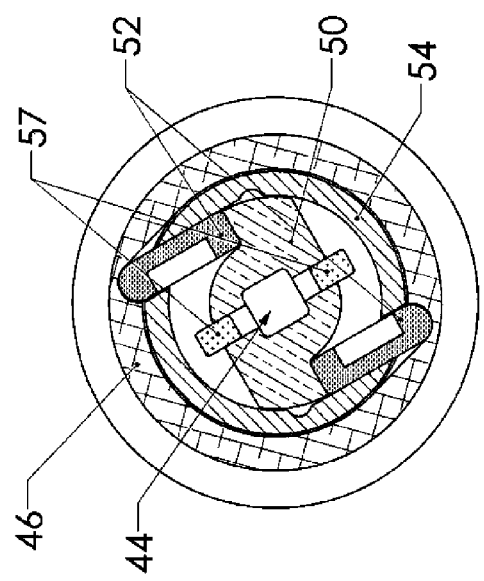
FIG.16

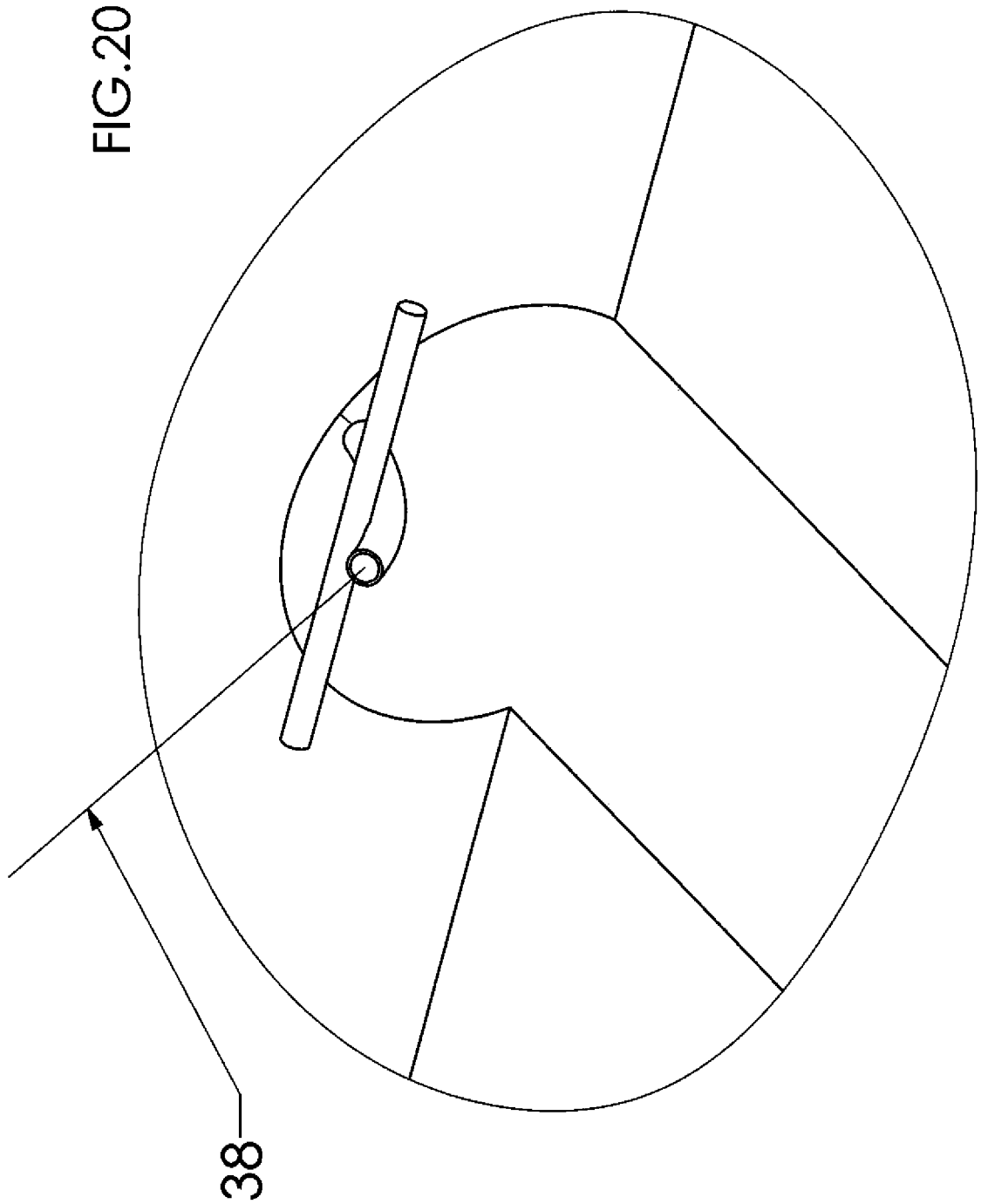

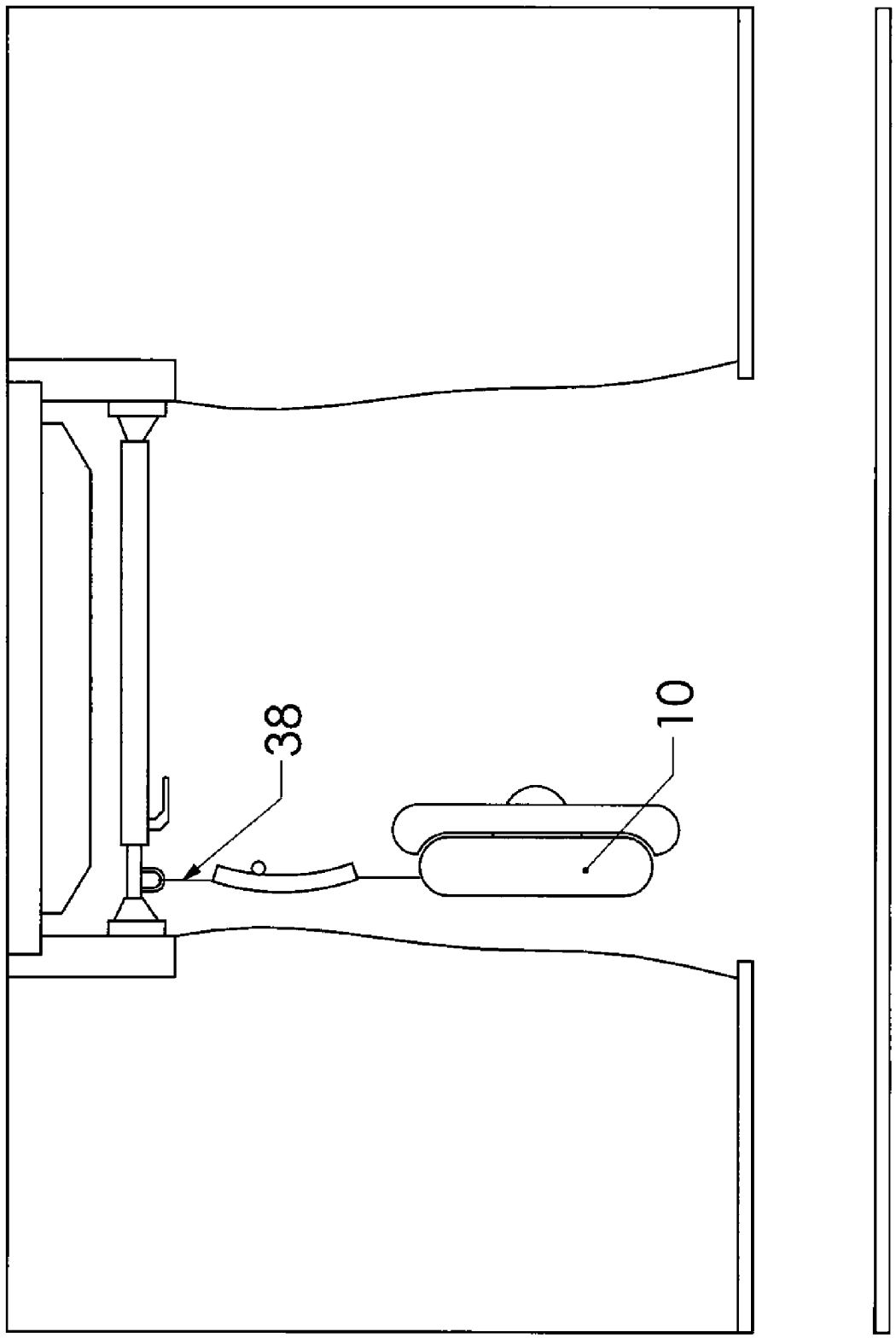

DEVICE FOR PIPE INSPECTION AND METHOD OF USING SAME

CROSS-REFERENCE TO RELATED APPLICATION

This application claims the benefit under 35 U.S.C. §119 (e) of the earlier filing date of U.S. Provisional Patent Application No. 61/110,870 filed on Nov. 3, 2008.

BACKGROUND

This application discloses an invention which is related, generally and in various embodiments, to devices utilized for pipe inspection and a method of using the same.

Information from water and sewage pipes has immense environmental, civil, and commercial value. Often, such environments are space constrained and generally ill-suited for people to access and labor. In some instances, compact, sensory-tailored robotic systems are utilized to gather information associated with the pipe environment.

A variety of circumstances can cause the robot's performance to be less than adequate. For example, as illustrated in FIG. 1, robots 62 which utilize wheels 60 or narrow tracks often encounter debris 61 or other obstacles in the pipe 59 which the robot 62 is unable to navigating past or through. In many situations, the wheels 60 or narrow tracks of the robot 62 do not come in contact with the debris 61 in the center of the pipe 59. In such situations, the robot 62 is not able to climb over the debris 61 and continue its movement.

Also, as illustrated in FIG. 2, when robots 62 which utilize wheels 60 attempt to navigate past or through hard debris 61 or other obstacles in a pipe, the robot 62 can become immobile and stuck in a "high centered" position. Once the front of the robot 62 drives over the hard debris 61 or obstacle, the front wheels are often lifted and provide no traction for the robot 62. Additionally, as most of the robot weight is transferred directly to the debris 61 or obstacle, the rear wheels do not have much weight applied to them, and generally are unable to provide enough force to create any further movement of the robot 62 in the pipe 59. Robots which utilize narrow tracks generally experience similar problems when the debris or obstacle is positioned between the tracks, either in front of or below the body.

Robots which utilize a conventional track and pulley system often suffer from jamming of the track system 68, thereby rendering the robot immobile. As shown in FIG. 3, the pulley 69 generally defines a continuous series of teeth and valleys around the circumference of the pulley, and the track 70 defines a continuous series of teeth and valleys which cooperatively engage with teeth and valleys of the pulley. With this configuration, even small particulate can cause large problems. Any particulate that enters the system and settles in a valley of either the pulley or the track can cause meshing problems between the track and the pulley once the particulate reaches the pulley-track interface. The particulate in the valley operates to lift the track off of the pulley, thereby placing an increased tension on the track, requiring the motor to work harder and harder to move the track, and potentially causing the jamming of the track system.

In many configurations, compact robots utilized to explore, navigate, map, etc. include a winch mounted to the exterior of the robot. The winch is utilized to reel in the tether, thereby pulling the robot back towards its starting position. Because the tether often operates to carry power and/or control data to the robot, and data from the robot to a device external to the pipe for processing, the tether tends to be relatively large and heavy, thereby adding unnecessary size and weight to the robot. In addition, as shown in FIG. 4, the capstan is typically a flat-bottomed capstan which facilitates cable movement in only one direction. With the flat capstan profile, the tether often tends to walk to one side and become tangled as it is run continuously.

For exterior mounted winch configurations, odometry is traditionally performed by a mechanical counter in contact with the pulley so that the counter increments its count with each revolution of the pulley. In order to avoid corrosion and other problems with the counter, the winch typically requires that a seal be utilized to isolate the counter from the environment in the pipe.

Leaving a manhole cover in an open position for any length of time while the robot is gathering information can also result in the robot's performance being less than ideal. Inside typical underground pipe systems, the temperature is relatively constant (e.g., around 50 degrees Fahrenheit), and the humidity is relatively constant and relatively high. When a manholes cover is left in an open position, cold surface air typically enters the pipe, and a dense fog can form due to the relatively high temperature and humidity of the existing air in the pipe. The fog can be so dense that it can prevent proper visual observation of the pipe wall, thereby preventing some defects from being observed.

SUMMARY

In one general respect, this application discloses a device. According to various embodiments, the device includes a sensor portion and a chassis portion. The sensor portion includes a plurality of sensing devices. The chassis portion is connected to the sensor portion and includes a first track and a second track. The second track is positioned adjacent the first track. The first and second tracks cooperate to substantially cover an entire width of the chassis portion.

In another general respect, this application discloses a method for inspecting an interior of a pipe. The method is implemented by a device. According to various embodiments, the method includes traversing the pipe, and capturing data associated with the pipe while the pipe is being traversed. The traversing and the capturing are performed by the device while a manhole through which the device gained access to the pipe is closed.

Aspects of the invention may be implemented by a computing device and/or a computer program stored on a computer-readable medium. The computer-readable medium may comprise a disk, a device, and/or a propagated signal.

BRIEF DESCRIPTION OF THE DRAWINGS

Various embodiments of the invention are described herein in by way of example in conjunction with the following figures, wherein like reference characters designate the same or similar elements.

FIG. 3 illustrates a conventional toothed pulley-track arrangement of a robot;
FIGS. 7 and 8 illustrate exploded views of a chassis portion of the robot of FIG. 5 according to various embodiments;

FIG. 16 illustrates the relationship of a capstan and a clutch of the winch assembly of FIG. 13 in various operating modes;

FIGS. 18-21 illustrate the robot of FIG. 5 at various stages of deployment.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

Figure 1:
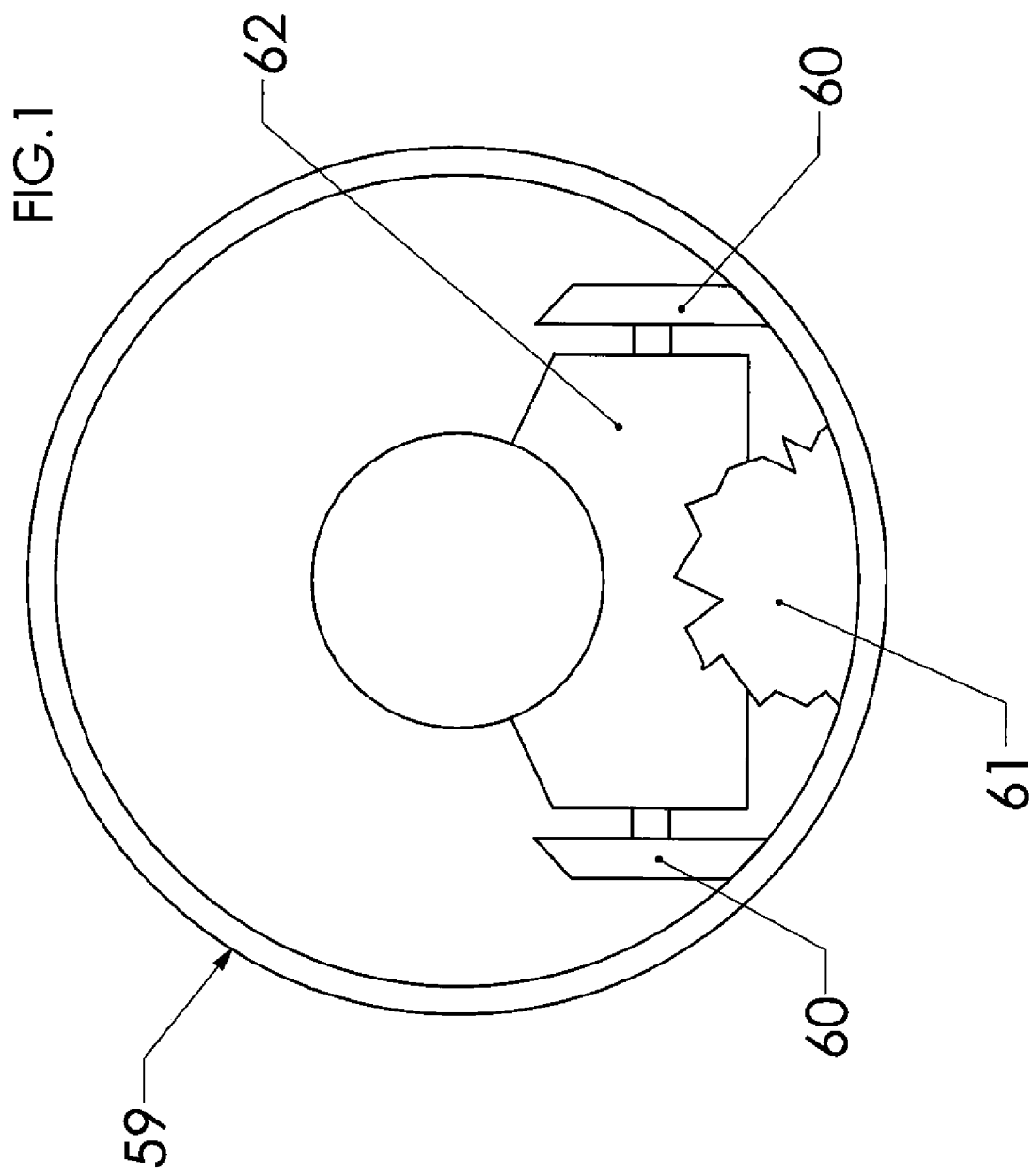
FIG. 1 illustrates a conventional wheeled robot.
Figure 2:
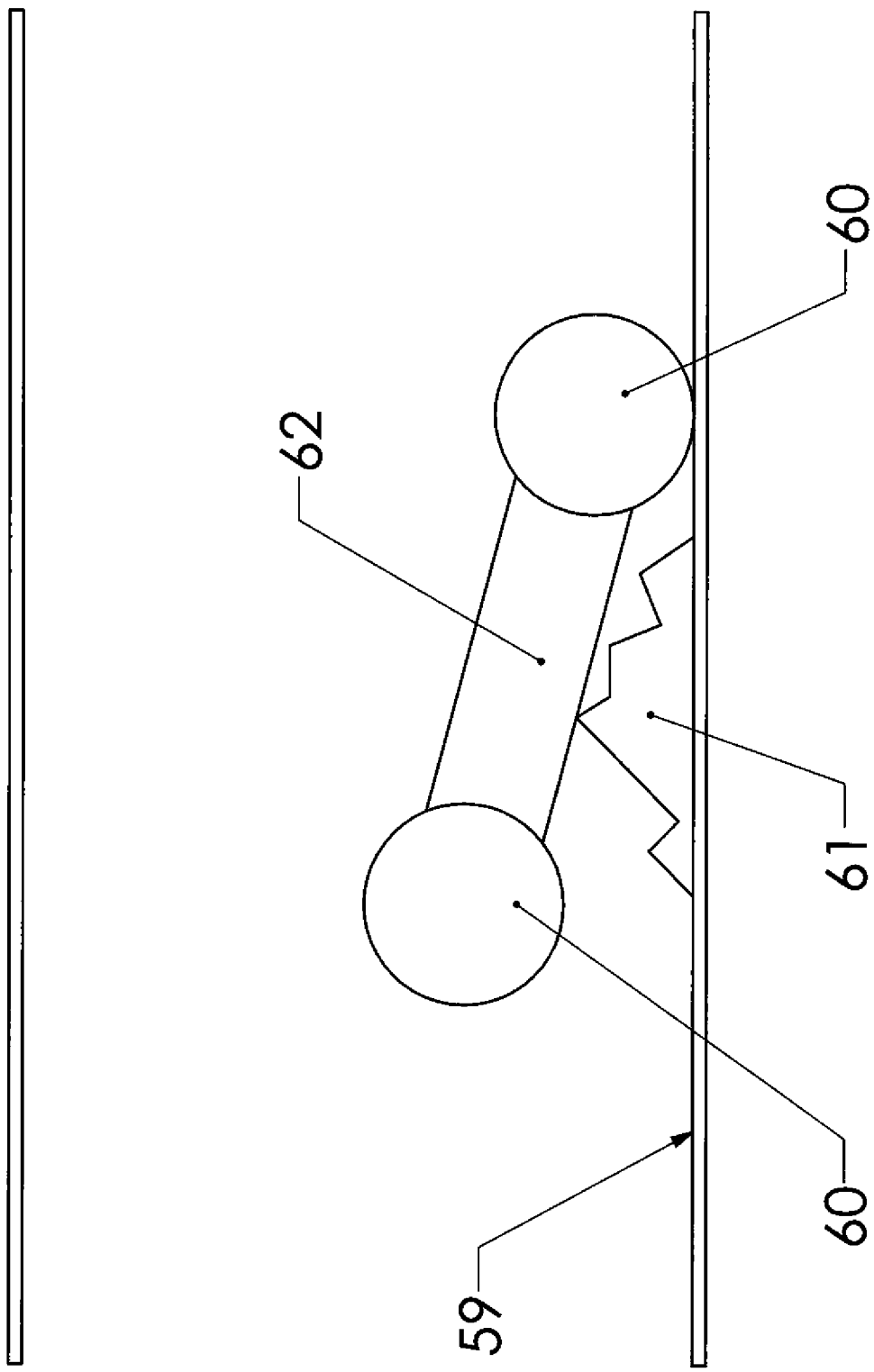
FIG. 2 illustrates a conventional wheeled robot.
Figure 4:
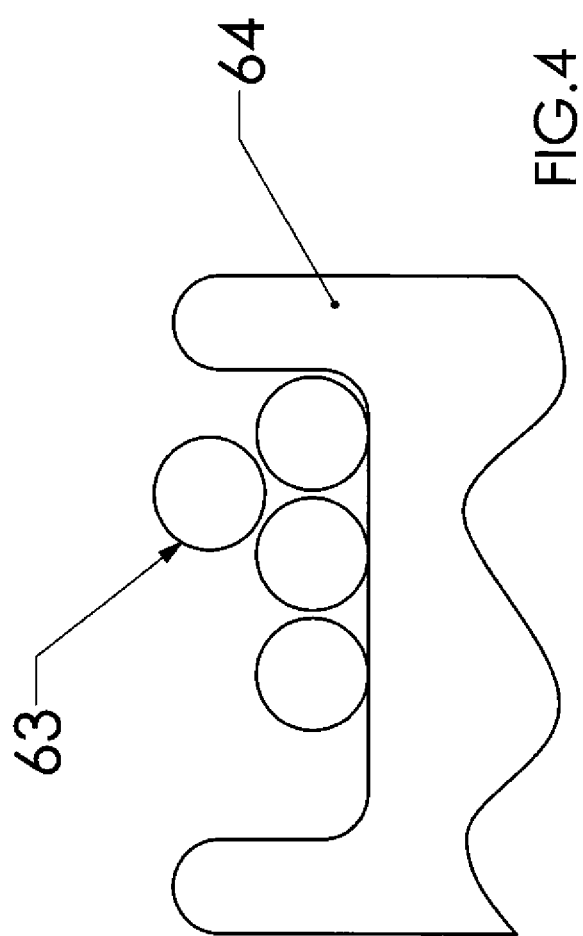
FIG. 4 illustrates a flat capstan profile of a winch.
Figure 5:
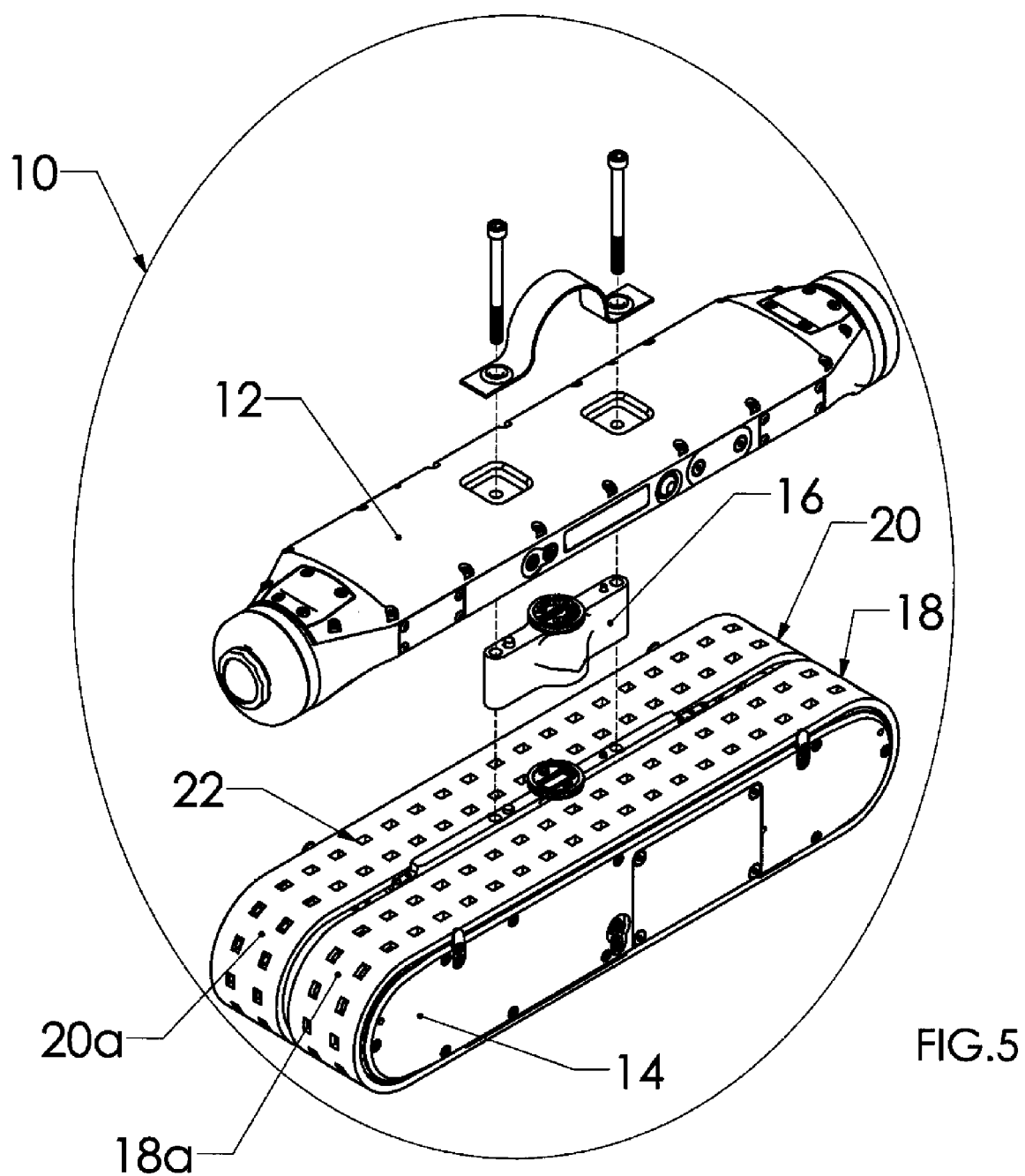
FIG. 5 illustrates various embodiments of an autonomous mobile robot.

FIG. 5 illustrates various embodiments of a device 10. For purposes of clarity, a partially exploded view of the device 10 is shown in FIG. 5. As explained in more detail hereinafter, the device may be utilized to navigate, explore, map, etc. various environments (e.g., water pipes, sewer pipes, etc.). For purposes of simplicity, the device 10 will be described in the context of an autonomous mobile robot 10 utilized for pipe inspection (e.g., a sewer pipe). However, it will be appreciated that the device 10 may be embodied in any number of different types of inspection platforms, including non-autonomous devices and tele-operated inspection platforms, and may be utilized in a plurality of other environments.

The autonomous mobile robot 10 includes a sensor portion 12 and a chassis portion 14. The sensor portion 12 is electrically and mechanically connected to the chassis portion 14. As shown in FIG. 5, the autonomous mobile robot 10 may also include a riser portion 16 which is positioned between the sensor portion 12 and the chassis portion 14, and is electrically and mechanically connected to each. The riser portion 16 operates to increase the distance the sensor portion 12 is situated above the lowest portion of the pipe, and may be utilized in large pipe applications to provide a desired vantage point for various sensing devices of the sensor portion 12. According to other embodiments, the autonomous mobile robot 10 does not include the above-described riser portion 16. Aspects of the autonomous mobile robot 10 may be implemented by a computing device and/or a computer program stored on a computer-readable medium. The computer-readable medium may comprise a disk, a device, and/or a propagated signal.

According to various embodiments, the sensor portion 12 includes a plurality of sensing devices (e.g., a camera, a radar device, a sonar device, an infrared device, a laser device, etc.) for sensing the conditions within the environment, a computing device communicably connected to the sensing devices and having a processor for processing raw information captured by the sensing devices, a memory device communicably connected to the computing device for storing the raw and/or processed information, and control circuitry communicably connected to the computing device for controlling various components of the autonomous mobile robot 10. The memory device may also be utilized to store software which is utilized by the autonomous mobile robot 10 to navigate, explore, map, etc. the environment.

As shown in FIG. 5, the chassis portion 14 includes a first track 18, and a second track 20. According to various embodiments, the first track 18 is identical to the second track 20. The first and second tracks 18, 20 may be fabricated from any suitable material or combination of materials, and may be fabricated as belts. According to various embodiments, the first and second tracks 18, 20, are fabricated from bonded elastic synthetic rubbers and polymers, and may additionally include steel or other members placed within or on the rubbers and polymers to increase their strength. The first and second tracks 18, 20 each define a plurality of openings 22 therethrough. The openings 22 may be of any suitable shape and size, and may be arranged in any suitable configuration. Although only two rows of the openings 22 are shown in FIG. 5 for each track, it is understood that the openings 22 may be arranged in any number of rows. The first track 18 is positioned adjacent the second track 20. Collectively, the first and second tracks 18, 20 define a spacing therebetween, and cover substantially the entire "width" of the chassis portion 14. For example, according to various embodiments, the width of the chassis portion is approximately 100 millimeters, and the first and second tracks 18, 20 collectively cover approximately 92 of the 100 millimeters.

The first track 18 defines a first surface 18a and a second surface 18b (not shown) opposite the first surface 18a. According to various embodiments, the first surface 18a is the surface which comes in contact with an interior surface of a sewer pipe when the autonomous mobile robot 10 is being utilized for a sewer pipe application. According to various embodiments, the first surface 18a of the first track 18 is substantially smooth. Similarly, the second track 20 defines a first surface 20a and a second surface 20b (not shown) opposite the first surface 20a. According to various embodiments, the first surface 20a is the surface which comes in contact with an interior surface of a sewer pipe when the autonomous mobile robot 10 is being utilized for a sewer pipe application. According to various embodiments, the first surface 20a of the first track 20 is substantially smooth. The respective first surfaces 18a, 20a of the first and second tracks 18, 20 have a relatively high static coefficient of friction. For example, according to various embodiments, the static coefficient of friction of the respective first surfaces 18a, 20a is approximately 1.0. In general, the static coefficient of friction of the respective first tracks 18a, 20a is approximately 0.8 or greater, which allows for good adhesion between the tracks 18, 20 and the interior surface of the sewer pipe.

According to various embodiments, the respective second surfaces 18b, 20b of the first and second tracks 18, 20 are also substantially smooth. For such embodiments, the respective second surfaces 18b, 20b may have a static coefficient of friction which is identical to that of the respective first surfaces 18a, 20a. For embodiments where the respective first surfaces 18a, 20a and the respective second surfaces 18b, 20b of the first and second tracks 18, are substantially smooth, when the respective first surfaces 18a, 20a become too worn, the first and second tracks 18, 20 can be removed and rotated (e.g., the first track 18 takes the place of the second track 20, and the second track 20 takes the place of the first track 18). By taking this action, different edges of the first and second tracks 18, 20 are placed into contact with the interior surface of the sewer pipe. By changing which drive assembly the first and second tracks 18, 20 are utilized with, the usable life of the first and second tracks 18, 20 is effectively doubled.

The first and second tracks 18, 20 may be referred to as full coverage/wide tracks. Due to the collective width of the first and second tracks 18, 20 relative to the width of the chassis portion 14, the first and second tracks 18, 20 collectively form nearly the entire "front", "bottom" and "rear" surfaces of the chassis portion 14. Thus, when the autonomous mobile robot 10 encounters any debris or feature within the sewer pipe, the first surfaces 18a, 20a of the first and second tracks 18, 20 come in contact with the debris or feature. In contrast to wheeled robots and narrow track robots, the full coverage/wide tracks 18, 20 are configured to enable the autonomous mobile robot 10 to climb over the debris or feature and continue performing the inspection, navigation, mapping, etc. For example, since nearly the entire "front" surface of the autonomous mobile robot 10 is a moving track surface, any debris or feature of sufficient vertical size encountered in the pipe will first hit this moving track surface, and little if any will hit a static part of the chassis portion 14. Also, since nearly the entire "bottom" surface of the autonomous mobile robot 10 is this moving track surface, any encountered debris or feature below the autonomous mobile robot 10 will first hit this moving track surface, and little if any will hit a static part of the chassis portion 14. Additionally, nearly all of the weight of the autonomous mobile robot 10 passes through the moving full coverage/wide tracks 18, 20 to the encountered debris or feature. Therefore, the autonomous mobile robot 10 is configured to always continue driving as the full coverage tracks 18, 20 can not rotate without contacting something to react with and continue driving.

Figure 6:
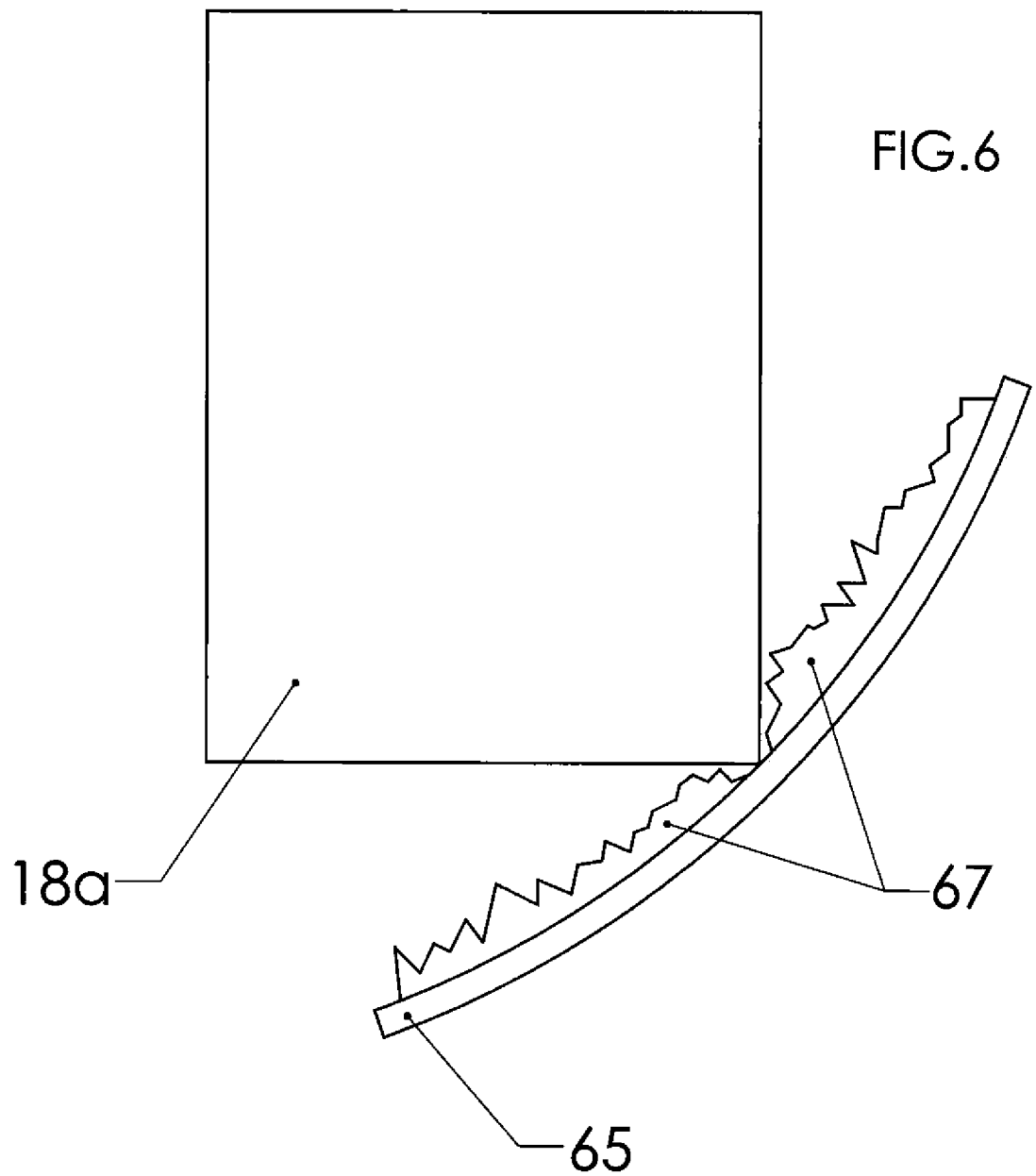
FIG. 6 illustrates a smooth outer edge of a track of the robot of FIG. 5.

FIG. 6 illustrates various embodiments of the first surface 18a of the first track 18 of the autonomous mobile robot 10. As explained hereinabove, the first and second tracks 18, 20 may be identical. For embodiments where the first surfaces 18a, 20a of the first and second tracks 18, 20 are substantially smooth, the first and second tracks 18, 20 have the unique ability to cut through grease deposits encountered in pipes (e.g., the grease deposit 67 shown in the pipe 65 in FIG. 6), thereby allowing for subsequent positive movement of the autonomous mobile robot 10. The respective first surfaces 18a, 20a are long and smooth, and generally have the entire weight of the autonomous mobile robot 10 applied to them. The weight, plus the continuous driving of the respective first surfaces 18a, 20a serve to operate as a squeegee or scraper, cutting through the layers of grease until the wall of the pipe is contacted. Once the wall of the pipe is contacted, the autonomous mobile robot 10 regains its traction, thereby allowing the movement and inspection to continue. Mobility platforms which include tracks having teeth or protuberances do not exhibit this ability. Every tooth valley acts as a collection chamber for the grease, picking it up and lying it back down. For such mobility platforms, the track never reaches the surface of the pipe because the track does not cut through the grease.

Figure 8:
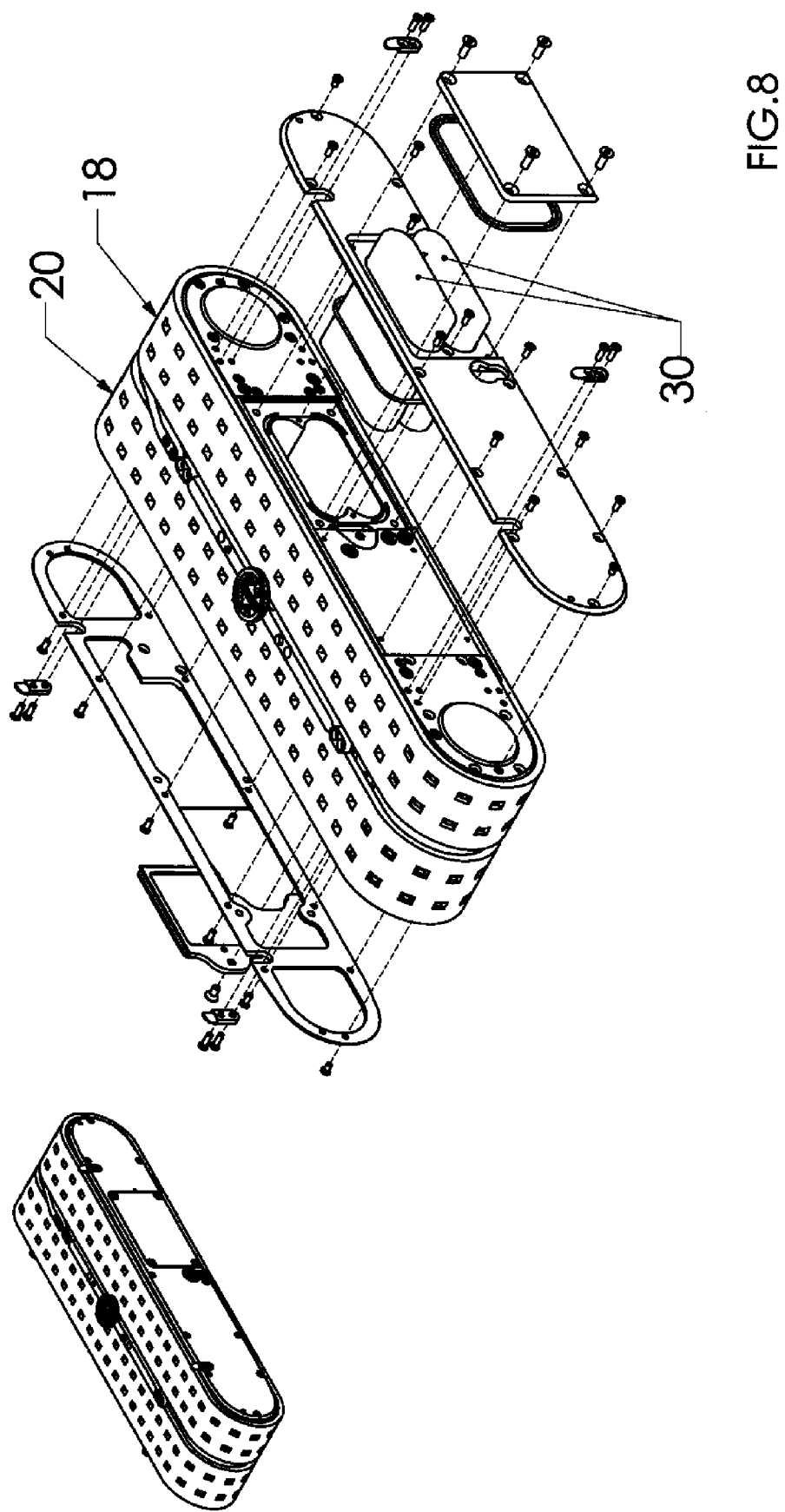

FIGS. 7 and 8 illustrate exploded views of the chassis portion 14 according to various embodiments. For purposes of clarity, the first and second tracks 18, 20 are not shown in FIG. 7. The chassis portion 14 includes a first drive assembly 24 and a second drive assembly 26. The chassis portion 14 also includes a reel system 27 (See FIG. 12) which includes a winch assembly 28, a payout assembly 59 (See FIG. 12), and a spindle assembly 29 (See FIG. 12). For purposes of clarity, the payout assembly 59 and the spindle assembly 29 are not shown in FIG. 7 or FIG. 8. The reel system 27 and its components will be described in more detail hereinafter. As shown in FIG. 8, the chassis portion 14 may also include one or more batteries 30 utilized to provide power to both the chassis portion 14 and the sensor portion 12. The location of the batteries 30 and the design of the panel behind which the batteries 30 are sealed allows for quick battery removal and replacement when needed. The chassis portion 14 further includes control circuitry communicably connected to the first and second drive assemblies 24, 26, and the reel system 27. The control circuitry operates to intelligently control the rotational speed and force of the first and second drive assemblies 24, 26, the winch assembly 28, and other components of the reel system 27.

Figure 9:
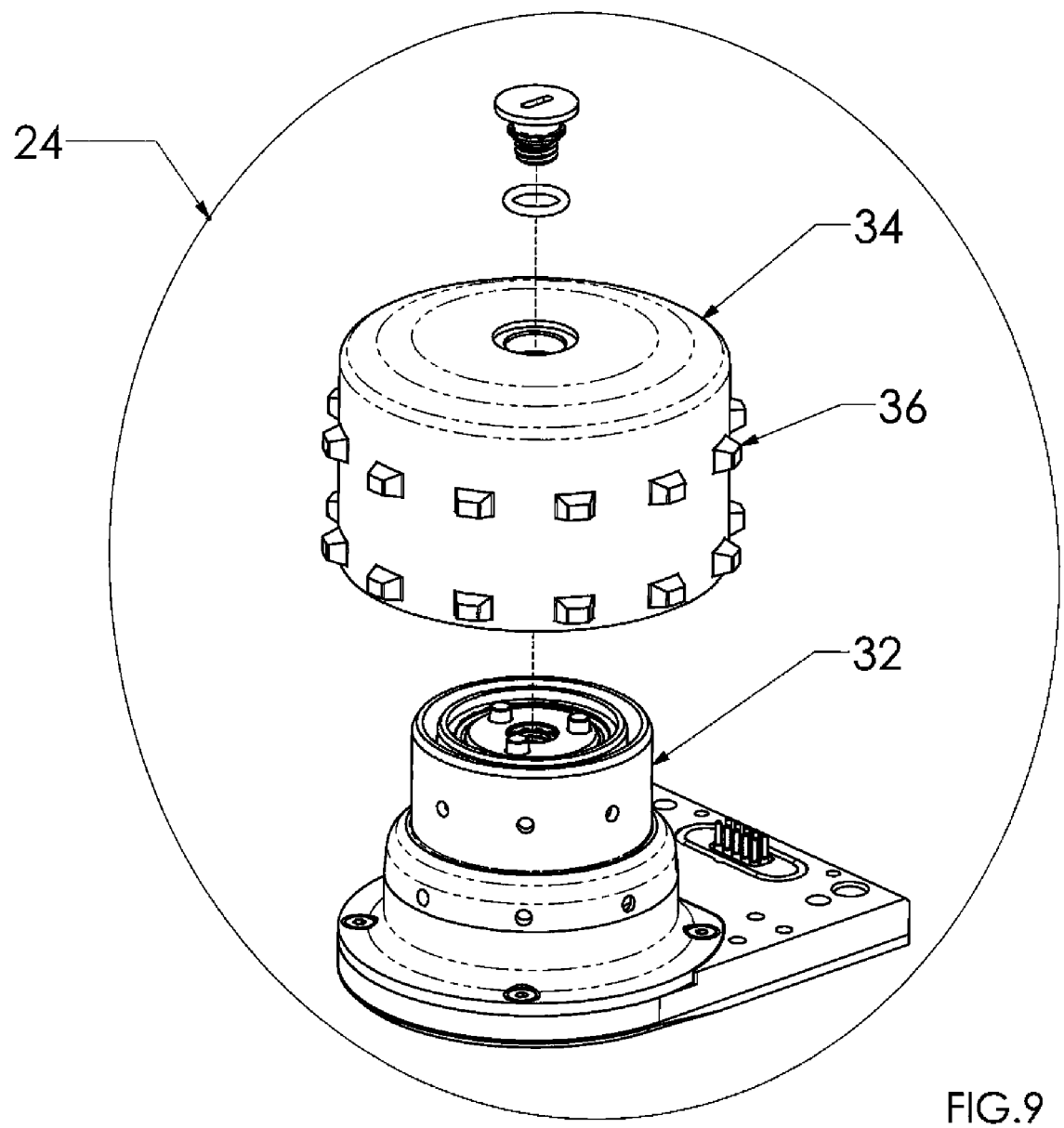
FIG. 9 illustrates an exploded view of a first drive assembly of the chassis portion of the robot of FIG. 5 according to various embodiments.
Figure 10:
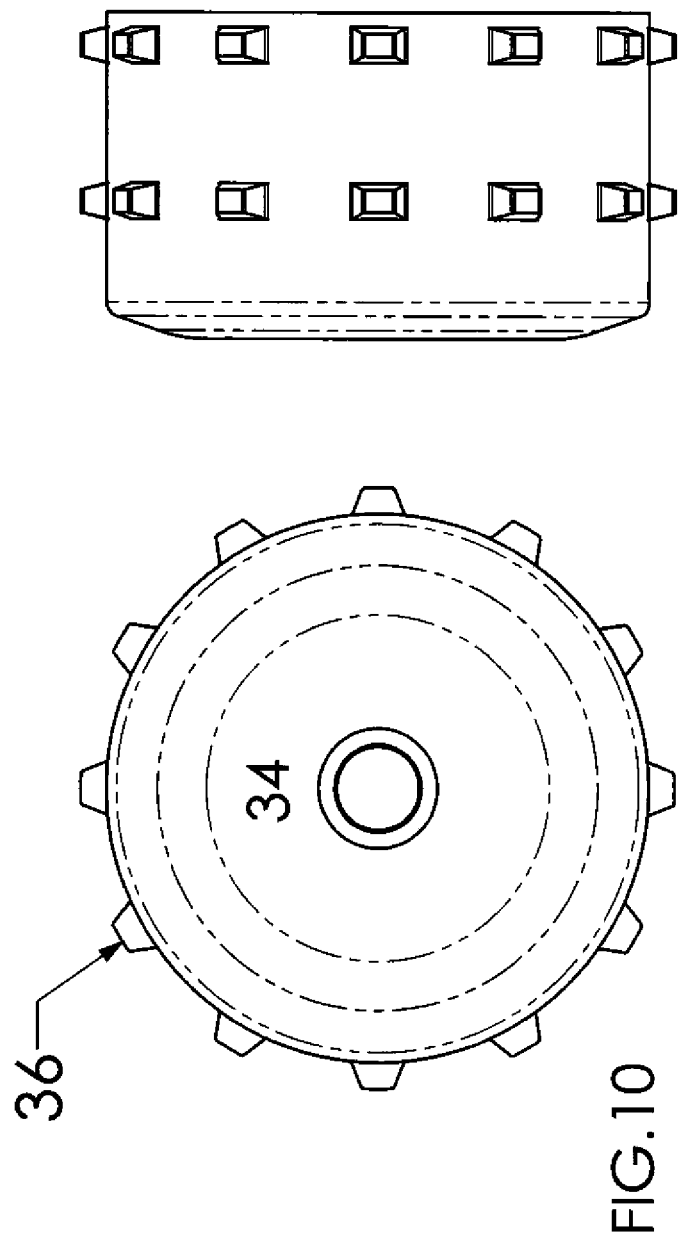
FIGS. 10 and 11 illustrate examples of studs of a pulley engaging with a track.

FIG. 9 illustrates an exploded view of the first drive assembly 24 according to various embodiments. According to various embodiments, the second drive assembly 26 is identical to the first drive assembly 24. As shown in FIG. 9, the first drive assembly 24 includes a drive motor 32 (and speed-reduction gear train), and a drive pulley 34 coupled to the motor 32. The drive pulley 34 includes a plurality of studs 36 (e.g., protuberances) which extend outward from a surface of the drive pulley 34. The studs 36 may be of any suitable size and shape, and may be arranged in any suitable configuration about the circumference of the drive pulley 34. According to various embodiments, the drive pulley 34 defines deep channels or grooves around the circumference of the pulley which operate to further allow any remaining particulate to be removed, thereby preventing the jamming of the first track 18. A given channel or groove may be positioned between the rows of studs 36, adjacent a given row of studs 36, etc. Although only two rows of studs 36 are shown in FIGS. 9 and 10, it will be appreciated that the studs 36 may be arranged in any number of rows. In general, the arrangements of the studs 36 and the openings 22 are compatible so that when the first track 18 is revolving around the chassis portion 14 (i.e., around the drive assembly 24, toward the winch assembly 28, around the winch assembly 28, and back toward the drive assembly 24) the studs 36 on the drive pulley 34 are engaged with openings 22 on the first track 18.

Figure 11:
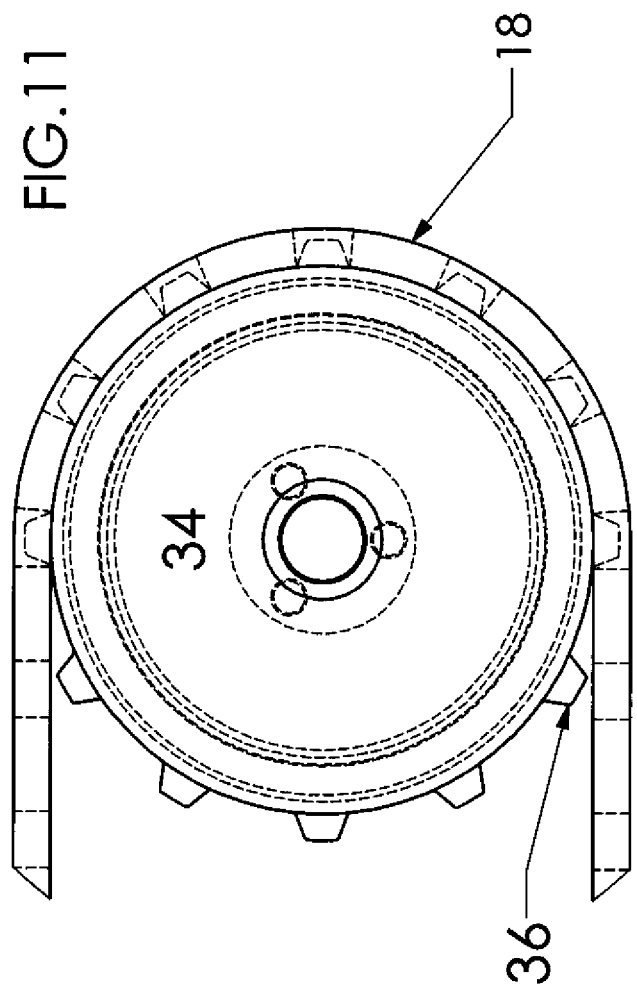

Examples of such an engagement are shown in FIG. 11. As shown in FIG. 11, when the studs 36 of the drive pulley 34 are engaged with the openings 22 defined by the first track 18, rotation of the drive pulley 34 in the "A" direction causes the first track 18 to rotate in the "A" direction, thereby moving the robot 10 forward. In the studded drive configuration, there are no small tooth valleys for particulates to collect and stay positioned in. Any particulate that ends up on the drive pulley 34 or the interior surface of the first track 18 can work its way out through the openings 22 in the first track 18 where the studs 36 mesh. Therefore, the first and second tracks 18, 20 may be considered to be self-cleaning tracks.

Due to the above-described drive assemblies 24, 26 and the self-cleaning full coverage/wide tracks 18, 20 of the autonomous mobile robot 10, the traditional pipe cleaning required prior to the deployment of wheeled robots and narrow track robots may not be necessary prior to the deployment of the autonomous mobile robot 10.

Figure 12:
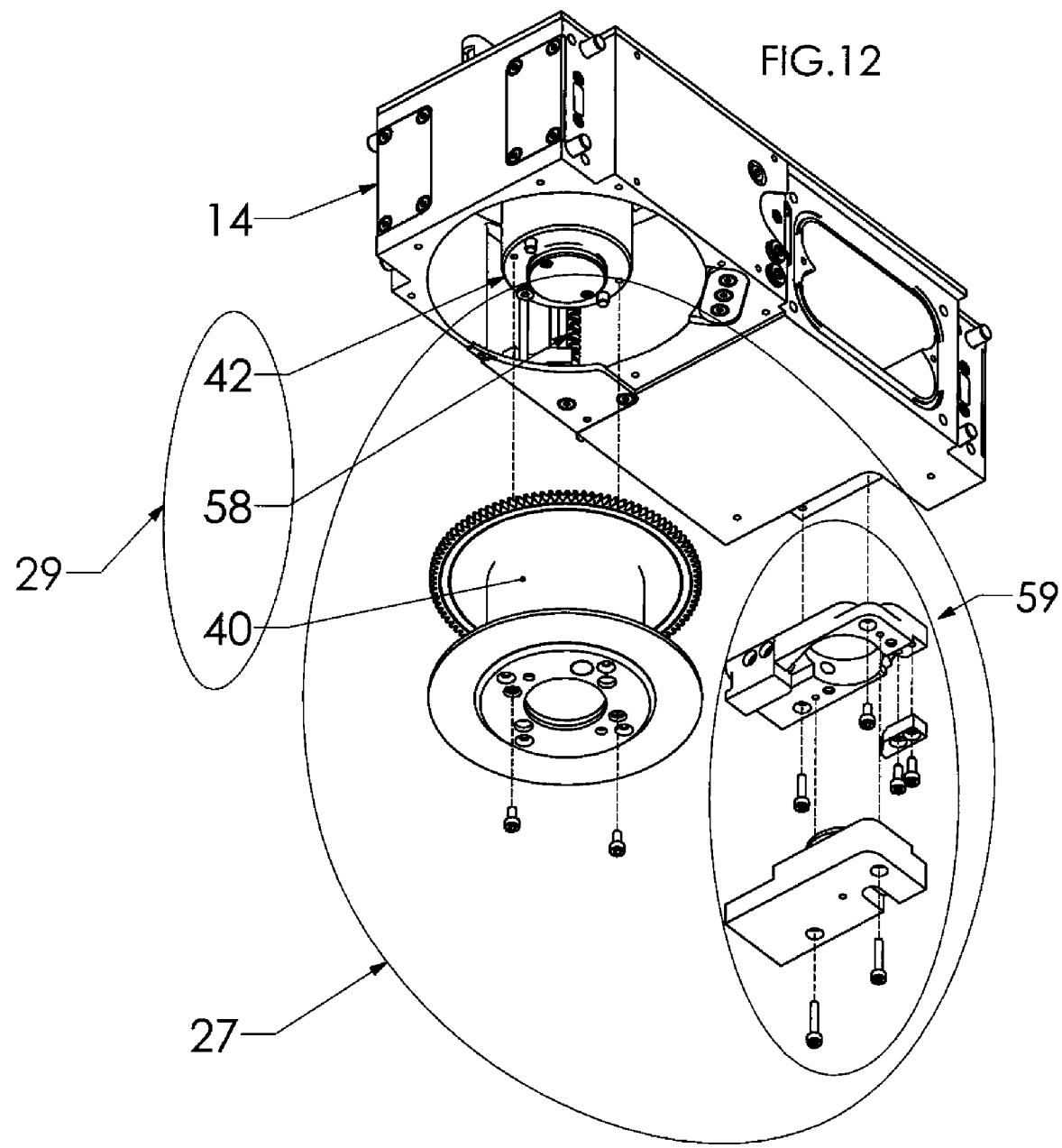
FIG. 12 illustrates an exploded view of a reel system of the chassis portion of the robot of FIG. 5 according to various embodiments.

FIG. 12 illustrates an exploded view of the reel system 27 according to various embodiments. The reel system 27 includes the winch assembly 28, the payout assembly 59, and the spindle assembly 29, all coupled together via a tether 38 (See FIG. 14). For purposes of clarity, the winch assembly 28 and the tether 38 are not shown in FIG. 12. As the robot 10 is autonomous, the tether 38 does not need to carry any power and/or data, and essentially serves as a lifeline. As a result, the tether 38 can be much smaller than a comparable tether which is utilized to carry power and/or data to a robot. According to various embodiments, the tether 38 is made of a braided synthetic fiber, but other embodiments could be made as a monofilament or braid of plastic or any other suitable material. Primary mechanical characteristics of the tether 38 may include low stretch under load (to minimize error of distance measurement), high breaking strength (to allow emergency extraction of the autonomous mobile robot 10 in the event it became stuck or wedged by dragging it out of the pipe through a manual or externally powered device), small bend radius and low susceptibility to kinking (to easy movement of the tether 38 in and out of the autonomous mobile robot 10), high chemical and environmental resistance (as the pipe environment is often corrosive, acidic, basic, salty, or possessing other hazardous characteristics and the outdoor environment possesses high ultraviolet radiation and extreme temperatures), and high resistance to wear (to minimize strength loss due to handling and rubbing of components of the pipe or autonomous mobile robot 10). As described in more detail hereinafter, the tether 38 may have a protective tiger tail connected thereto, and may also have a tiger tail bar connected thereto.

The spindle assembly 29 comprises a tether spindle 40, a drive motor 42 (and a speed-reduction gear train) connected to the tether spindle 40, and a levelwind system 58. As the tether 38 advances past the payout system 59, the tether 38 contacts the levelwind system 58 while passing therethrough, and is wrapped multiple times around the tether spindle 40. The length of tether 38 wrapped around the tether spindle 40 decreases as the robot 10 advances. The levelwind system 58 operates to lay the tether 38 onto the tether spindle 40 in an even manner, thereby preventing the tether 38 from bulging up at only one location on the tether spindle 40.

Figure 13:
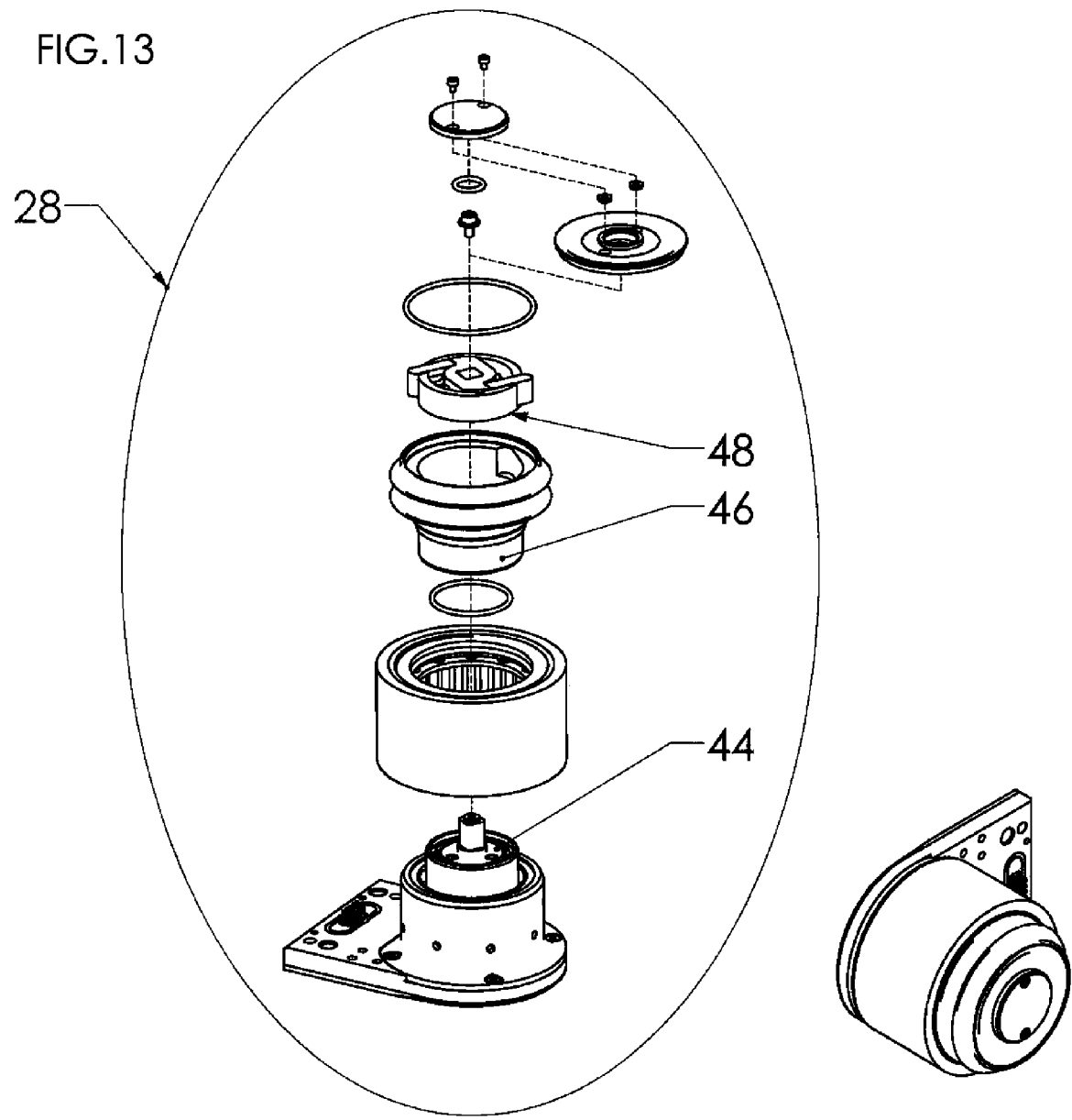
FIG. 13 illustrates an exploded view of the winch assembly of the chassis portion of the robot of FIG. 5 according to various embodiments.
Figure 14:
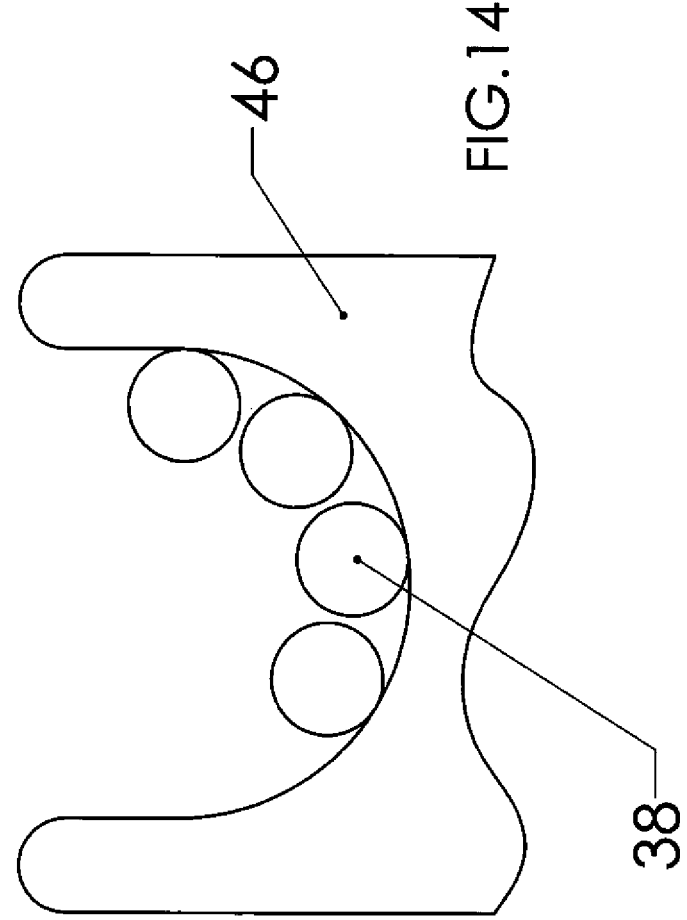
FIG. 14 illustrates various embodiments of a capstan of the winch assembly of FIG. 13.

FIG. 13 illustrates an exploded view of the winch assembly 28 according to various embodiments. The winch assembly 28 includes a drive motor 44 (and a speed-reduction gear train), a capstan drum 46, and a clutch 48. The capstan drum 46 is coupled through the clutch 48 to the motor 44. The motor 44 may have a higher torque than the motor 42. The winch assembly 28 may be utilized by the robot 10 to perform emergency self-extraction. The winch assembly 28 may also be utilized to allow the robot 10 to lift itself up out of a given pipe at the end of an inspection, exploration, mapping, etc. As the tether 38 enters the robot 10, the tether 38 is wrapped multiple times around the capstan 46 (e.g., for two, three, or four loops) and is generally under a constant tension between the tether spindle 40 and the capstan 46 through force provided by the motor 42. As shown in FIG. 14, the capstan 46 defines a curved profile (as opposed to a flat or coned profile) which operates to prevent the tether 38 from climbing up on itself and tangling.

Figure 15:
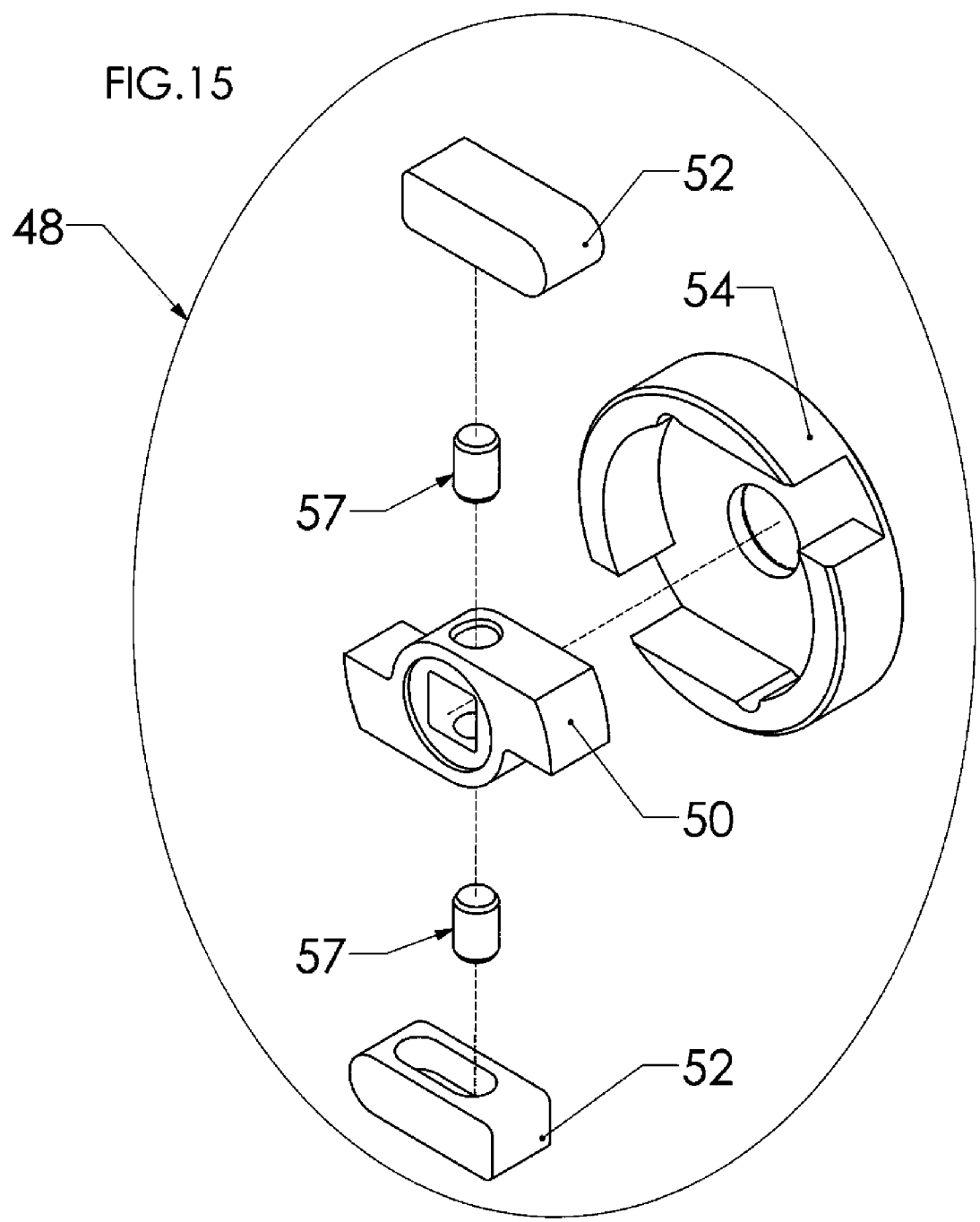
FIG. 15 illustrates an exploded view of a clutch of the winch assembly of FIG. 13 according to various embodiments.

FIG. 15 illustrates an exploded view of the clutch 48 according to various embodiments. The clutch 48 includes a drive cam 50, first and second drive keys 52, and a housing 54. When the autonomous mobile robot 10 advances, tether 38 exits the chassis portion 14 by way of several wraps around the capstan 46. Any movement of the tether 38 causes the capstan 46 to turn, and any other part of the autonomous mobile robot 10 connected to the tether 38. By disconnecting the motor 44 from the capstan 46 when the autonomous mobile robot 10 is moving forward, the capstan 46 is free to spin by itself and the motor 44 remains stationary. If the motor 44 were always connected to the capstan 46, it would be back driven by the tether 38 exiting the chassis 14, resulting in high parasitic drag. To achieve this disengagement, and the resultant lower parasitic drag without additional actuators, the motor 44 rotates in one direction which causes the drive cam 50 and its pins 57 to suck the drive keys 52 radially inward and within the outer diameter of the clutch housing 54. When the autonomous mobile robot 10 is moving backward and/or retrieving tether outside the autonomous mobile robot 10, the motor 44 rotates in the opposite direction. This causes the drive cam 50 to push the drive keys 52 radially outward, past the outer diameter of the housing 54 and into slots (not shown) the capstan 46. Once the keys 52 are in the capstan 46 slots, continued motor 44 rotation will result in rotation of the capstan 46 and powered retrieval of tether 38 outside the robot 10 to its interior. FIG. 16 illustrates the relationship of the capstan 46 and the clutch 48 in various operating modes—with the capstan 46 engaged, with the capstan 46 disengaging, and with the capstan 46 disengaged.

Figure 17:
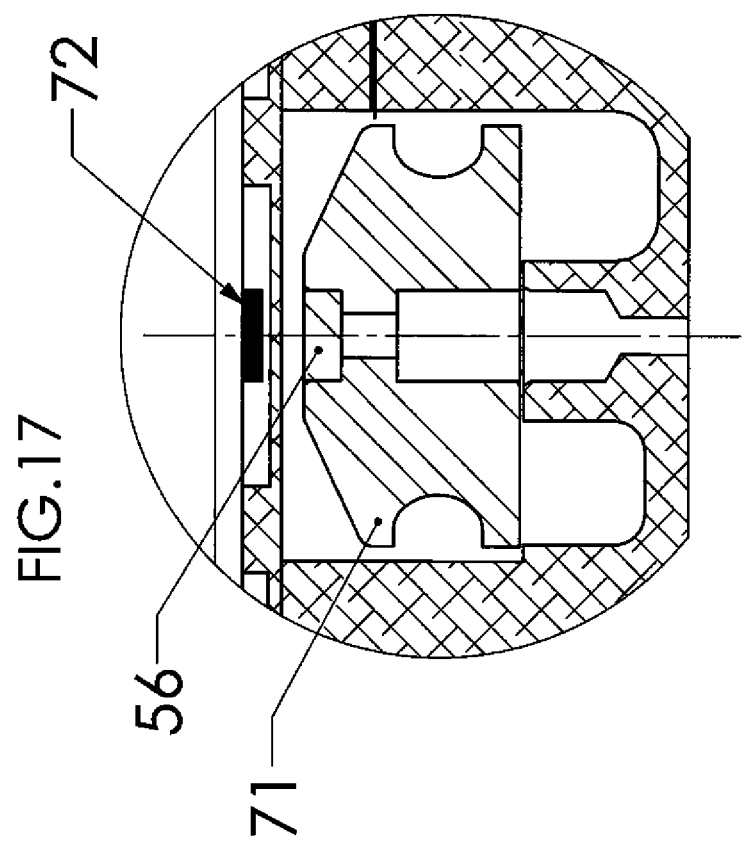
FIG. 17 illustrates various embodiments of a payout assembly of the chassis portion of the robot of FIG. 5.
Figure 18:
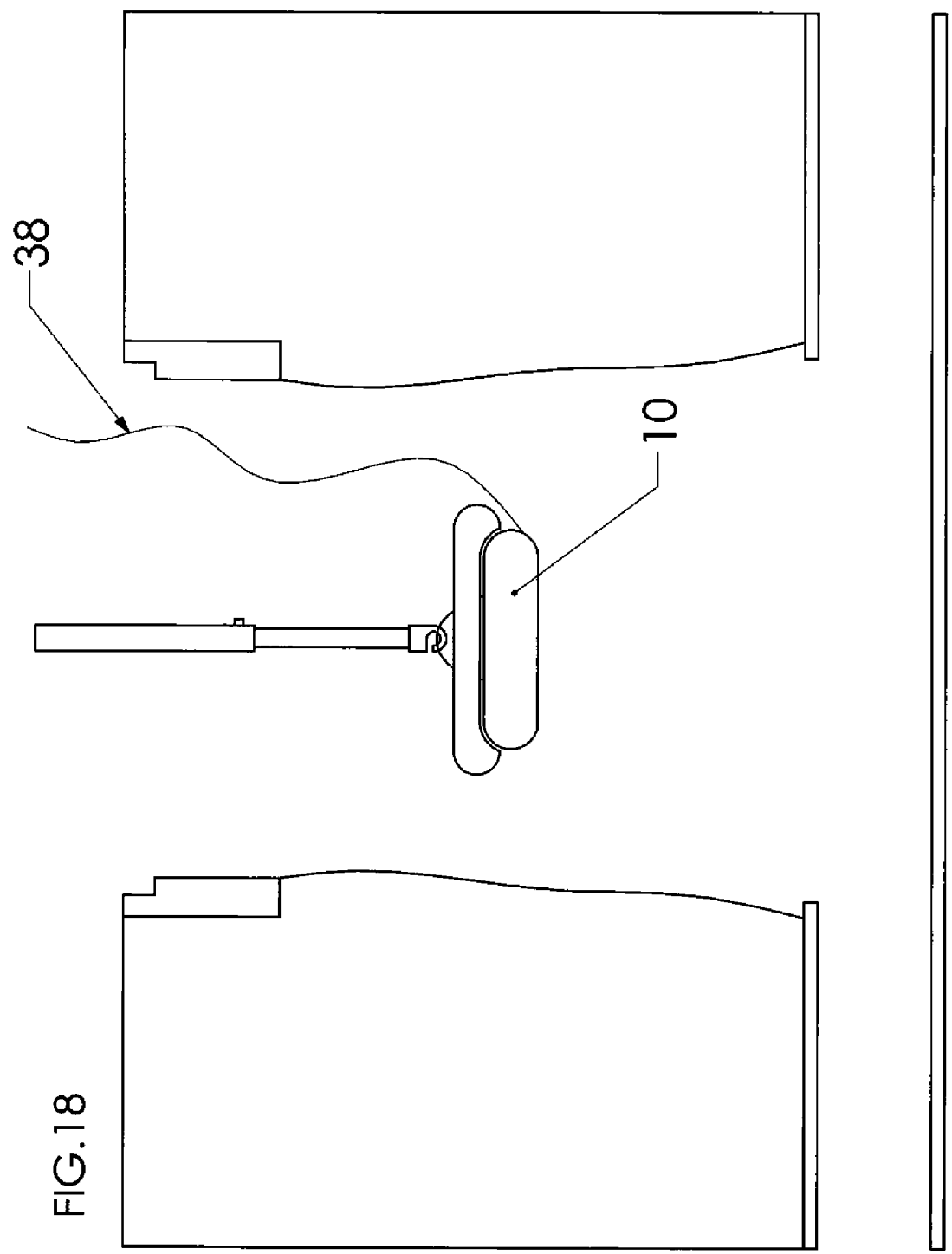
Figure 19:
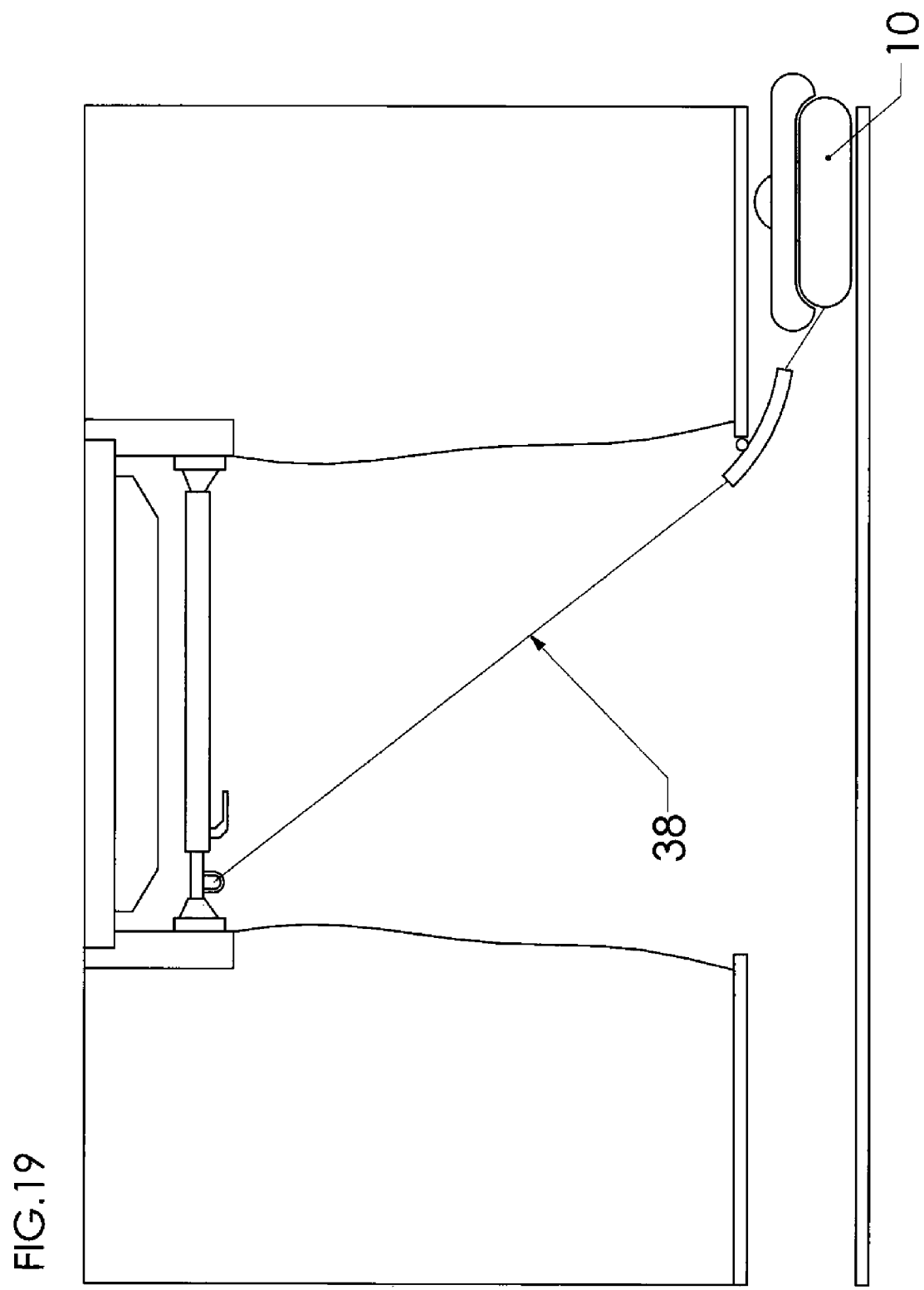

FIG. 17 illustrates various embodiments of the payout assembly 59. The payout assembly 59 includes an encoder magnet 56, a roller 71, and an encoder chip 72. As the tether 38 exits the capstan drum 46 of the winch assembly 28 in the direction of the spindle assembly 29, the tether 38 is wrapped around the roller 71 (e.g., wrapped once around the roller) before the tether 38 advances to the spindle assembly 29. The encoder magnet 56 is coupled to the roller 71 and is utilized by the autonomous mobile robot 10 to perform odometry or position measurement. As described in more detail hereinafter, the tether 38 is anchored at the insertion manhole and is drawn out of the autonomous mobile robot 10 as the autonomous mobile robot 10 advances while inspecting a target pipe. As the tether 38 enters or exits the chassis portion 14, the movement of the tether 38 turns the roller 71 that it is wrapped around. Therefore, movement and absolute linear position of the autonomous mobile robot 10 within the pipe may be measured by counting the number of rotations of the roller 71 via its coupled magnet 56. As the magnet 56 rotates, its magnetic field rotates and that rotation can be measured via the encoder chip 72, even through the solid wall of the chassis portion 14 between them. This non-contact payout mechanism has no shaft seal which could wear and fail or which could cause parasitic drag to the movement of the tether 38.

In contrast to traditional systems where the tether is pulled through the pipe from a reel external to the pipe, the autonomous mobile robot 10 lays tether 38 statically into the inspected pipe from the autonomous mobile robot 10. Therefore, the autonomous mobile robot 10 experiences much less drag from its tether 38 than traditional systems, resulting in increased mobility and capability in inspecting pipe. The autonomous mobile robot 10 is generally freed of towed-tether related drag and snag issues, allowing the autonomous mobile robot 10 to have equal or better mobility than traditional inspection platforms, while having a smaller & lighter physical profile and lower power consumption.

According to various embodiments, the robot 10 is approximately 500 millimeters in length, approximately 120 millimeters in width, and approximately 125 millimeters in height. The relatively compact physical size of the robot 10, when combined with the drive system described hereinabove, allows the robot 10 to bypass obstacles that a larger platform would be unable to traverse. According to various embodiments, the robot 10 is waterproof (e.g., to IP68 or better, and positively pressurized) so it can drive through flooded pipe bellies and is easily disinfected by immersion in a cleaning solution after use. According to various embodiments, the reel storage area, payout measurement area, and all passageways leading to and from are unsealed and flood when the robot 10 is submerged. For such embodiments, the rest of the robot 10, including the interiors of the chassis portion 14 and sensor portion 12, is isolated from the external environment through a combination of o-rings, shaft seal, and/or cured compounds.

FIGS. 18-21 illustrate the autonomous mobile robot 10 at various stages of deployment. The autonomous mobile robot 10 may be lowered through a manhole to gain access to a pipe needing inspection. According to various embodiments, a robot hanger (e.g., an in-chimney anchor) is secured in the chimney, and the tether 38 is coupled to the robot hanger, thereby coupling the autonomous mobile robot 10 to the robot hanger. The autonomous mobile robot 10 is then lowered to the bottom of the manhole and placed in front of the pipe to be inspected. According to various embodiments, the autonomous mobile robot 10 is placed via a telescoping deployment pole. The robot 10 may stay in a wait mode until some time after the manhole is closed or it may start its inspection immediately. For example, an internal timer of the robot 10 may be set to activate the inspection process at a future or optimal time. In either immediate or delayed inspection, the manhole can be closed once the robot 10 is lowered, which allows for road traffic to resume normal flow while the inspection is occurring. The crew is then able to leave the site and begin another deployment at another site with a second autonomous mobile robot 10, thereby increasing the productivity of the crew.

For instances where the manhole cover is in the closed position during the inspection, the pipe environment is isolated from the surface environment. By closing the manhole after the robot 10 is lowered, the amount of cold surface air which enters the pipe being inspected is limited, and the amount of fog produced by the cold surface air is similarly limited. Also, by delaying the start of the inspection until some period of time after the manhole is closed, any fog initially produced by the cold surface air can disperse, thereby providing the autonomous mobile robot 10 with better inspection conditions in the pipe. Additionally, by delaying the start of the inspection to perform the inspection at an optimal time (e.g., in the middle of the night when water levels are generally lowest), more of the pipe surfaces can be visually recorded and therefore more defects observed in subsequent analysis.

A tiger tail system may be installed around to the tether 38. The tiger tail system includes a sleeve, and a bar or other member coupled to the sleeve. Once the robot 10 is lowered to the pipe and begins to advance, the sleeve operates to prevent the tether 38 from fraying due to contact with an edge of the pipe where the bottom of the chimney meets the opening of the pipe. The sleeve may be fabricated from any suitable material (e.g., plastic), and the tether 38 passes therethrough. The bar or other member is generally perpendicular to the sleeve, has a length which is greater than the diameter of the pipe, and operates to properly position the sleeve relative to the pipe opening. In contrast to the traditional installation by a member of the crew at the edge of the pipe opening, the tiger tail system is self installing. When the robot 10 advances into the pipe, the sleeve is pulled into place and the bar is pulled across the pipe opening, thereby securing the sleeve in place without the assistance of a crew member.

Once the pipe inspection is completed, the winch assembly 28 may be utilized to return the robot 10 back to the starting manhole, where the winch assembly 28 then operates to automatically lift the robot 10 up out of the bottom of the manhole and into the chimney where it hangs until it is retrieved. By removing itself from the pipe and the bottom of the manhole, the robot 10 removes itself as a potential impediment to flow within the pipe and manhole. The retrieval of the robot 10 can take place at any time later, at the convenience of the crew, and is a simple matter of opening the manhole and lifting out the suspended waiting robot 10 by removing the hanger. According to other embodiments, the autonomous mobile robot 10 can drive back to the starting manhole while retrieving tether 38 and wait at the bottom of the manhole for the crew to return. For such embodiments, the crew may retrieve the robot 10 by removing the hanger and then using the telescoping deployment pole to lift the robot 10 out from the manhole.

Nothing in the above description is meant to limit the invention to any specific materials, geometry, or orientation of elements. Many part/orientation substitutions are contemplated within the scope of the invention and will be apparent to those skilled in the art. The embodiments described herein were presented by way of example only and should not be used to limit the scope of the invention.

Although the invention has been described in terms of particular embodiments in this application, one of ordinary skill in the art, in light of the teachings herein, can generate additional embodiments and modifications without departing from the spirit of, or exceeding the scope of, the described invention. Accordingly, it is understood that the drawings and the descriptions herein are proffered only to facilitate comprehension of the invention and should not be construed to limit the scope thereof.

What is claimed is:

1. A device, comprising:
a sensor portion, wherein the sensor portion comprises a plurality of sensing devices; and
a chassis portion connected to the sensor portion, wherein the chassis portion comprises:
a first track; and
a second track positioned adjacent the first track, wherein the first and second tracks cooperate to substantially cover an entire width of the chassis portion.

2. The device of claim 1, wherein the plurality of sensing devices comprise at least two of the following:
a camera;
a radar device;
a sonar device;
an infrared device; and
a laser device.

3. The device of claim 1, wherein:
the first track defines a first plurality of openings therethrough; and
the second track defines a second plurality of openings therethrough.

4. The device of claim 1, wherein:
at least one surface of the first track is substantially smooth; and
at least one surface of the second track is substantially smooth.

5. The device of claim 1, wherein:
the at least one surface of the first track has a static coefficient of friction which is at least 0.8; and
the at least one surface of the second track has a static coefficient of friction which is at least 0.8.

6. The device of claim 1, wherein the chassis portion further comprises:
a first drive assembly, wherein the first drive assembly is in contact with the first track; and
a second drive assembly positioned adjacent the first drive assembly, wherein the second drive assembly is in contact with the second track.

7. The device of claim 6, wherein the first drive assembly comprises:
a motor;
a speed reduction gear train connected to the motor; and
a drive pulley connected to the speed reduction gear train.

8. The device of claim 7, wherein the drive pulley defines a plurality of studs.

9. The device of claim 8, wherein the plurality of studs are configured to mate with a plurality of openings defined by the first track.

10. The device of claim 7, wherein the drive pulley defines at least one groove around a circumference of the drive pulley.

11. The device of claim 10, wherein the at least one groove is positioned between a first stud defined by the drive pulley and a second stud defined by the drive pulley.

12. The device of claim 1, further comprising a riser portion connected to the sensor portion and the chassis portion.

* * * * *